(12) United States Patent
Cuthbertson et al.

(10) Patent No.: US 10,792,113 B2
(45) Date of Patent: Oct. 6, 2020

(54) INTERFACING A SURGICAL ROBOT AND INSTRUMENT

(71) Applicant: CMR Surgical Limited, Cambridge (GB)

(72) Inventors: Rebecca Anne Cuthbertson, Cambridge (GB); Ben Robert Chaplin, Cambridge (GB); Keith Marshall, Cambridge (GB); Luke David Ronald Hares, Cambridge (GB); Nikki Priyam Su-Ling Phoolchund, Cambridge (GB)

(73) Assignee: CMR SURGICAL LIMITED, Cambridge (GB)

( * ) Notice: Subject to any disclaimer, the term of this patent is extended or adjusted under 35 U.S.C. 154(b) by 166 days.

(21) Appl. No.: 16/060,587

(22) PCT Filed: Dec. 9, 2016

(86) PCT No.: PCT/GB2016/053893
§ 371 (c)(1),
(2) Date: Jun. 8, 2018

(87) PCT Pub. No.: WO2017/098266
PCT Pub. Date: Jun. 15, 2017

(65) Prior Publication Data
US 2018/0353251 A1    Dec. 13, 2018

(30) Foreign Application Priority Data
Dec. 10, 2015  (GB) .................................. 1521808.4

(51) Int. Cl.
*A61B 34/35*      (2016.01)
*A61B 34/00*      (2016.01)
(Continued)

(52) U.S. Cl.
CPC .............. *A61B 34/35* (2016.02); *A61B 17/32* (2013.01); *A61B 34/30* (2016.02); *A61B 34/71* (2016.02);
(Continued)

(58) Field of Classification Search
CPC ......... A61B 17/29; A61B 34/35; A61B 34/30; A61B 34/71; A61B 2034/306; A61B 2034/301
See application file for complete search history.

(56) References Cited

U.S. PATENT DOCUMENTS 5,582,617 A * 12/1996 Klieman ................ A61B 17/29
                                                              606/170
5,649,956 A *  7/1997 Jensen ................... B25J 9/1065
                                                              403/316
(Continued)

FOREIGN PATENT DOCUMENTS

WO    2011123669 A1    10/2011
WO    2014162217 A1    10/2014
(Continued)

OTHER PUBLICATIONS

International Search Report and Written Opinion from corresponding PCT/GB2016/053893 dated Feb. 20, 2017.
(Continued)

*Primary Examiner* — Melanie R Tyson
(74) *Attorney, Agent, or Firm* — Lando & Anastasi, LLP

(57) ABSTRACT

A robotic surgical instrument comprising: a shaft; an articulation at a distal end of the shaft for articulating an end effector, the articulation driveable by a pair of driving elements; and an instrument interface at a proximal end of the shaft, the instrument interface comprising an instrument interface element for driving the pair of driving elements, the instrument interface element displaceable over a first
(Continued)

displacement range, the instrument interface element comprising a body receivable in a drive assembly interface element of a robot arm when the robotic surgical instrument engages with the surgical robot arm, the drive assembly interface element displaceable over a second displacement range, the length of the body in the displaceable direction being greater than one of the maximum travel of the body over the first displacement range and the maximum travel of the drive assembly interface element over the second displacement range.

20 Claims, 24 Drawing Sheets

(51) Int. Cl.
*A61B 34/30* (2016.01)
*A61B 17/32* (2006.01)
*A61B 17/00* (2006.01)
*A61B 18/00* (2006.01)

(52) U.S. Cl.
CPC ............... *A61B 2017/00398* (2013.01); *A61B 2017/00477* (2013.01); *A61B 2018/00172* (2013.01); *A61B 2034/301* (2016.02); *A61B 2034/306* (2016.02)

(56) References Cited

U.S. PATENT DOCUMENTS

| | | | | |
|---|---|---|---|---|
| 6,206,903 B1* | 3/2001 | Ramans | ................. | A61B 17/29 606/205 |
| 6,312,435 B1* | 11/2001 | Wallace | ................. | A61B 34/70 606/130 |
| 6,554,844 B2* | 4/2003 | Lee | ...................... | A61B 5/0084 606/1 |
| 6,676,684 B1* | 1/2004 | Morley | ................. | A61B 34/71 606/205 |
| 8,961,533 B2* | 2/2015 | Stahler | ................. | A61B 34/30 606/108 |
| 2013/0172713 A1 | 7/2013 | Kirschenman | | |
| 2015/0265355 A1 | 9/2015 | Prestel et al. | | |

FOREIGN PATENT DOCUMENTS

| | | | | |
|---|---|---|---|---|
| WO | 2015175200 A1 | 11/2015 | | |
| WO | WO-2015175200 A1 * | 11/2015 | ....... | A61B 17/00234 |
| WO | 2016183054 A1 | 11/2016 | | |

OTHER PUBLICATIONS

United Kingdom Search Report from corresponding United Kingdom Application No. GB1620994.2 dated May 11, 2017.

* cited by examiner

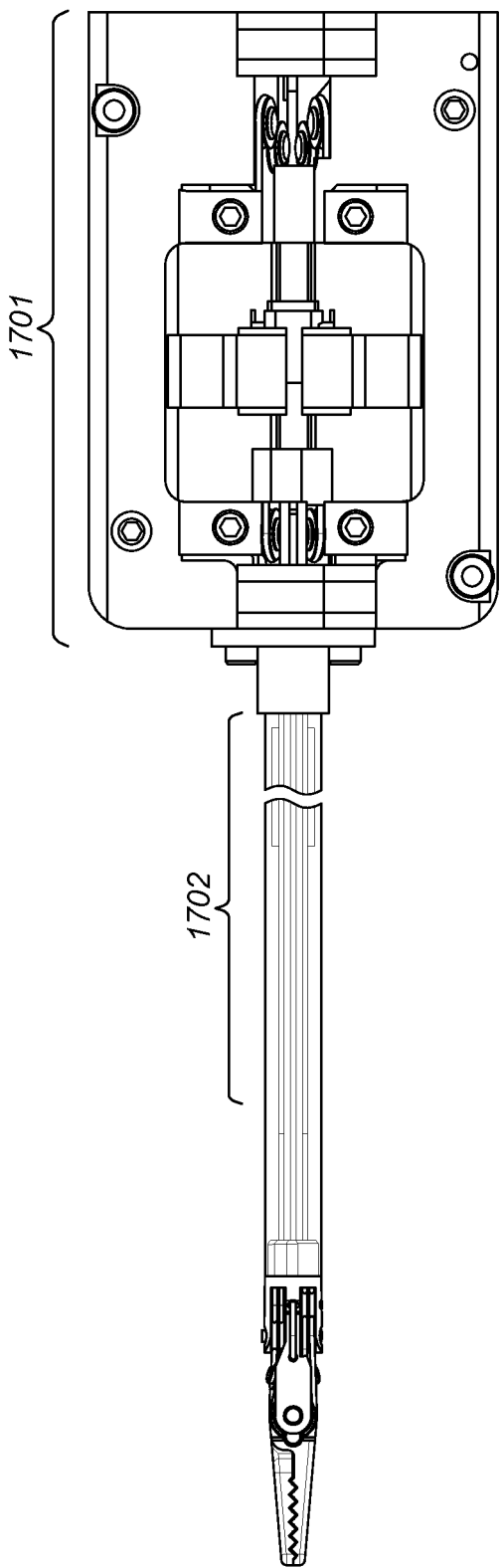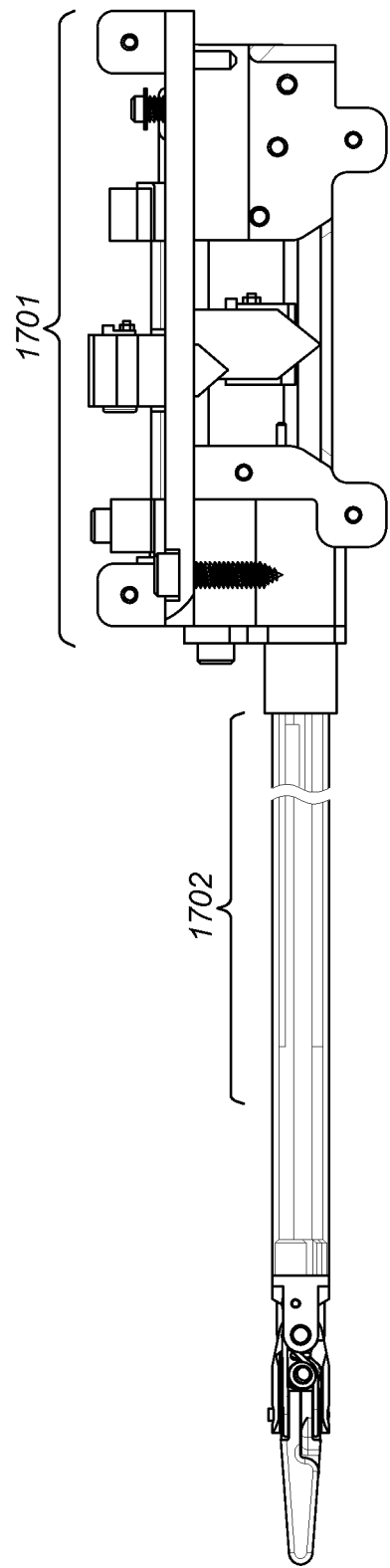
FIG. 17a
FIG. 17b

INTERFACING A SURGICAL ROBOT AND INSTRUMENT

CROSS-REFERENCE TO RELATED APPLICATIONS

This application is a U.S. National Phase Application under 35 U.S.C. § 371 of International Application No. PCT/GB2016/053893, filed Dec. 9, 2016, which claims priority to United Kingdom Application No. 1521808.4, filed Dec. 10, 2015, which is hereby incorporated by reference in its entirety for all purposes.

BACKGROUND

It is known to use robots for assisting and performing surgery. FIG. 1 illustrates a typical surgical robot 100 which consists of a base 108, an arm 102, and an instrument 105. The base supports the robot, and is itself attached rigidly to, for example, the operating theatre floor, the operating theatre ceiling or a trolley. The arm extends between the base and the instrument. The arm is articulated by means of multiple flexible joints 103 along its length, which are used to locate the surgical instrument in a desired location relative to the patient. The surgical instrument is attached to the distal end 104 of the robot arm. The surgical instrument penetrates the body of the patient 101 at a port 107 so as to access the surgical site. At its distal end, the instrument comprises an end effector 106 for engaging in a medical procedure.

FIG. 2 illustrates a typical surgical instrument 200 for performing robotic laparoscopic surgery. The surgical instrument comprises a base 201 by means of which the surgical instrument connects to the robot arm. A shaft 202 extends between base 201 and articulation 203. Articulation 203 terminates in an end effector 204. In FIG. 2, a pair of serrated jaws are illustrated as the end effector 204. The articulation 203 permits the end effector 204 to move relative to the shaft 202. It is desirable for at least two degrees of freedom to be provided to the motion of the end effector 204 by means of the articulation.

FIG. 3 illustrates an example of a known surgical instrument 300 in which end effector 204 is permitted to move relative to shaft 202 by means of pitch joint 301 and two yaw joints 302. Joint 301 enables the end effector 204 to rotate about pitch axis 303. Joints 302 enable each jaw of the end effector 204 to rotate about yaw axis 304. The joints are driven by cables 306, 307 and 308. Pulley 305 is used to direct cables 307 and 308 from their passage over the pitch joint to the yaw joints. Pulley 305 is offset from the central axis of the articulation 203. The external diameter of the shaft is 8 mm in order to accommodate the number, size and location of the internal elements of the articulated portion.

It is desirable to reduce the external diameter of the instrument in order to minimise the size of the incision through the skin of the patient and minimise disruption inside the patient's body. It is also desirable to minimise the weight of the surgical instrument so as to minimise the size and weight of the robot base and arm required to support the instrument, thereby enabling the robot as a whole to be more compact and hence occupy a smaller space in the operating theatre and be more moveable within the operating theatre.

In a typical laparoscopy operation, a surgeon utilises many instruments, and hence exchanges one instrument for another many times. It is therefore desirable to minimise the time taken and maximise the ease with which one instrument is detached from a robot arm and a different instrument is attached. Additionally, it is desirable to minimise the time taken in setting up the instrument ready for use once it has been attached to the robot arm.

SUMMARY OF THE INVENTION

According to an aspect of the invention, there is provided a robotic surgical instrument as set out in the accompanying claims.

At least one aspect of the invention is directed to a robotic surgical instrument comprising a shaft, an articulation at a distal end of the shaft for articulating an end effector, the articulation driveable by a pair of driving elements, and an instrument interface at a proximal end of the shaft, the instrument interface comprising an instrument interface element for driving the pair of driving elements, the instrument interface element displaceable over a first displacement range, the instrument interface element comprising a body receivable in a drive assembly interface element of a robot arm when the robotic surgical instrument engages with the surgical robot arm, the drive assembly interface element displaceable over a second displacement range, the length of the body in the displaceable direction being greater than one of the maximum travel of the body over the first displacement range and the maximum travel of the drive assembly interface element over the second displacement range.

According to one embodiment, the length of the body in the displaceable direction is greater than both the maximum travel of the body over the first displacement range and the maximum travel of the drive assembly interface element over the second displacement range. In one embodiment, the first displacement range is the same as the second displacement range. In another embodiment, the second displacement range is parallel to the first displacement range. In one embodiment, the first displacement range is parallel to a longitudinal axis of the shaft.

According to another embodiment, the body comprises lower sidewalls separated by the length of the body in the displaceable direction and upper sidewalls which taper from the lower sidewalls. In one embodiment, the upper sidewalls are configured to insert into the drive assembly interface element prior to the lower sidewalls on engaging the robotic surgical instrument with the robot arm. In another embodiment, the upper sidewalls taper to a point. In one embodiment, the upper sidewalls taper symmetrically to a point. In another embodiment, the upper sidewalls taper to a point meeting at an angle of less than or the same as 80°.

According to one embodiment, the upper sidewalls taper from the lower sidewalls to a roller, the roller configured to rotate about an axis perpendicular to the displaceable direction. In one embodiment, the roller is located on the point of the body.

According to another embodiment, the robotic surgical instrument comprises a roller attached to each upper sidewall, each roller configured to rotate about an axis perpendicular to the displaceable direction. In one embodiment, the lower sidewalls are perpendicular to the displaceable direction.

According to one embodiment, the maximum travel of the body over the first displacement range is half the length of the body. In one embodiment, the maximum travel of the drive assembly interface element over the second displacement range is half the length of the body. In another embodiment, the pair of driving elements is fast with the instrument interface elements such that displacement of the instrument interface element is transferred to the pair of driving elements.

Another c surgical robot arm comprising a drive assembly at a distal end of the surgical robot arm, the drive assembly comprising a drive assembly interface element for driving an instrument interface element of a robotic surgical instrument when the surgical robot arm engages with the robotic surgical instrument, the drive assembly interface element displaceable over a second displacement range, the drive assembly interface element comprising a socket configured to receive a body of the instrument interface element, the instrument interface element displaceable over a first displacement range, the internal length of the socket in the displaceable direction being greater than one of the maximum travel of the body over the first displacement range and the maximum travel of the socket over the second displacement range.

According to one embodiment, the length of the socket in the displaceable direction is greater than both the maximum travel of the body over the first displacement range and the maximum travel of the socket over the second displacement range. In one embodiment, the first displacement range is the same as the second displacement range. In another embodiment, the first displacement range is parallel to the second displacement range. In one embodiment, the socket comprises sidewalls separated by the length of the body in the displaceable direction, the sidewalls each terminating in a roller, each roller configured to rotate about an axis perpendicular to the displaceable direction.

According to another embodiment, the sidewalls are perpendicular to the displaceable direction. In one embodiment, the maximum travel of the socket over the second displacement range is half the length of the socket. In another embodiment, the maximum travel of the body over the first displacement range is half the length of the socket.

At least one aspect of the invention is directed to a surgical robot comprising a robotic surgical instrument comprising a shaft, an articulation at a distal end of the shaft for articulating an end effector, the articulation driveable by a pair of driving elements, and an instrument interface at a proximal end of the shaft, the instrument interface comprising an instrument interface element for driving the pair of driving elements, the instrument interface element displaceable over a first displacement range, the instrument interface element comprising a body, and a surgical robot arm comprising a drive assembly at a distal end of the surgical robot arm, the drive assembly comprising a drive assembly interface element for driving the instrument interface element when the surgical robot arm engages with the robotic surgical instrument, the drive assembly interface element displaceable over a second displacement range, the drive assembly interface element comprising a socket configured to receive the body, wherein the length of the body in the displaceable direction is greater than one of the maximum travel of the body over the first displacement range and the maximum travel of the drive assembly interface element over the second displacement range.

According to one embodiment, the length of the body in the displaceable direction is greater than both the maximum travel of the body over the first displacement range and the maximum travel of the drive assembly interface element over the second displacement range. In one embodiment, the first displacement range is the same as the second displacement range. In another embodiment, the second displacement range is parallel to the first displacement range. In one embodiment, the first displacement range is parallel to a longitudinal axis of the shaft.

According to another embodiment, the body comprises lower sidewalls separated by the length of the body in the displaceable direction, and upper sidewalls which taper from the lower sidewalls. In one embodiment, the upper sidewalls are configured to insert into the drive assembly interface element prior to the lower sidewalls on engaging the robotic surgical instrument with the robot arm. In another embodiment, the upper sidewalls taper to a point. In one embodiment, the upper sidewalls taper symmetrically to a point. In another embodiment, the upper sidewalls taper to a point meeting at an angle of less than or the same as 80°.

According to one embodiment, the upper sidewalls taper from the lower sidewalls to a roller, the roller configured to rotate about an axis perpendicular to the displaceable direction. In one embodiment, the roller is located on the point of the body.

According to another embodiment, the surgical robot further comprises a roller attached to each upper sidewall, each roller configured to rotate about an axis perpendicular to the displaceable direction. In one embodiment, the lower sidewalls are perpendicular to the displaceable direction.

According to one embodiment, the maximum travel of the body over the first displacement range is half the length of the body. In one embodiment, the maximum travel of the drive assembly interface element over the second displacement range is half the length of the body. In another embodiment, the pair of driving elements is fast with the instrument interface elements such that displacement of the instrument interface element is transferred to the pair of driving elements. In one embodiment, the internal length of the socket in the displaceable direction is greater than one of the maximum travel of the body over the first displacement range and the maximum travel of the socket over the second displacement range.

According to another embodiment, the length of the socket in the displaceable direction is greater than both the maximum travel of the body over the first displacement range and the maximum travel of the socket over the second displacement range. In one embodiment, the socket comprises socket sidewalls separated by the length of the body in the displaceable direction, the socket sidewalls each terminating in a roller, each roller configured to rotate about an axis perpendicular to the displaceable direction. In another embodiment, the socket sidewalls are perpendicular to the displaceable direction. In one embodiment, the maximum travel of the socket over the second displacement range is half the length of the socket. In another embodiment, the maximum travel of the body over the first displacement range is half the length of the socket.

BRIEF DESCRIPTION OF THE FIGURES

The present invention will now be described by way of example with reference to the accompanying drawings. In the drawings:

FIGS. 17a and 17b illustrate two views of a surgical instrument;

DETAILED DESCRIPTION

Figure 4:
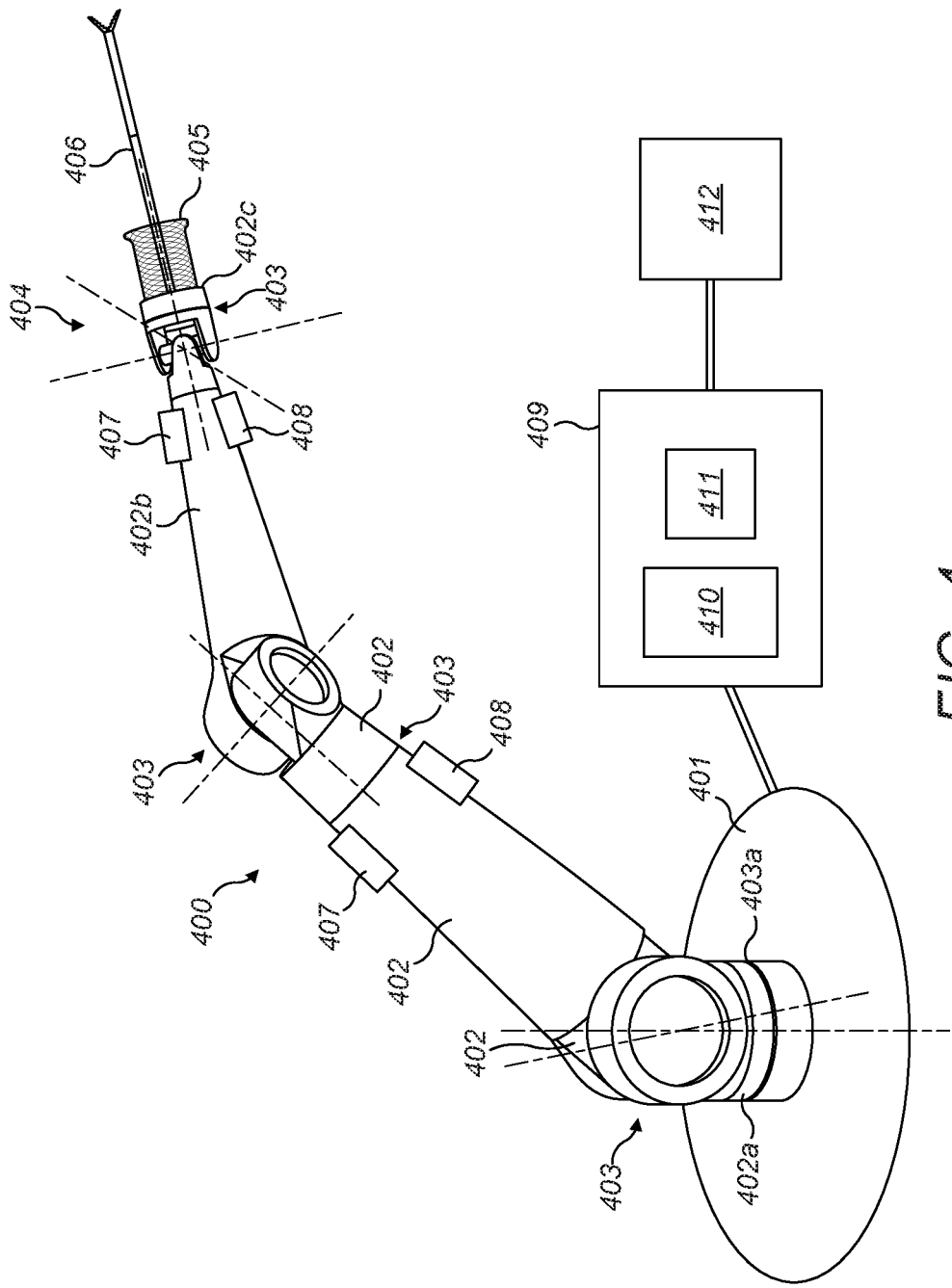
FIG. 4 illustrates a surgical robot.

FIG. 4 illustrates a surgical robot having an arm 400 which extends from a base 401. The arm comprises a number of rigid limbs 402. The limbs are coupled by revolute joints 403. The most proximal limb 402a is coupled to the base by joint 403a. It and the other limbs are coupled in series by further ones of the joints 403. Suitably, a wrist 404 is made up of four individual revolute joints. The wrist 404 couples one limb (402b) to the most distal limb (402c) of the arm. The most distal limb 402c carries an attachment 405 for a surgical instrument 406. Each joint 403 of the arm has one or more motors 407 which can be operated to cause rotational motion at the respective joint, and one or more position and/or torque sensors 408 which provide information regarding the current configuration and/or load at that joint. Suitably, the motors are arranged proximally of the joints whose motion they drive, so as to improve weight distribution. For clarity, only some of the motors and sensors are shown in FIG. 4.

Figure 1:
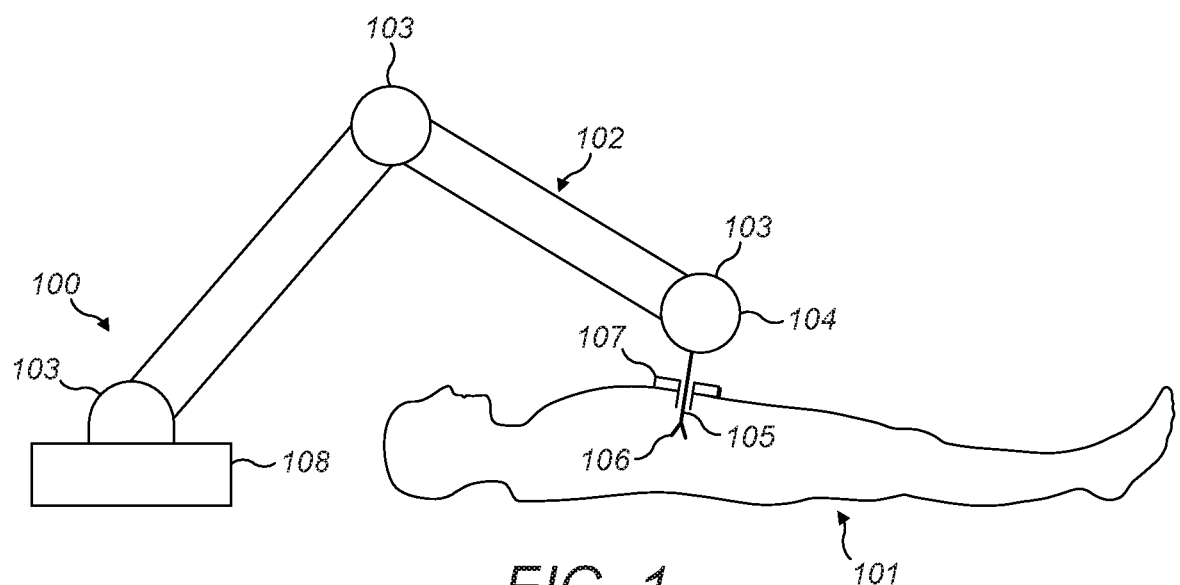
FIG. 1 illustrates a surgical robot performing a surgical procedure.
Figure 2:
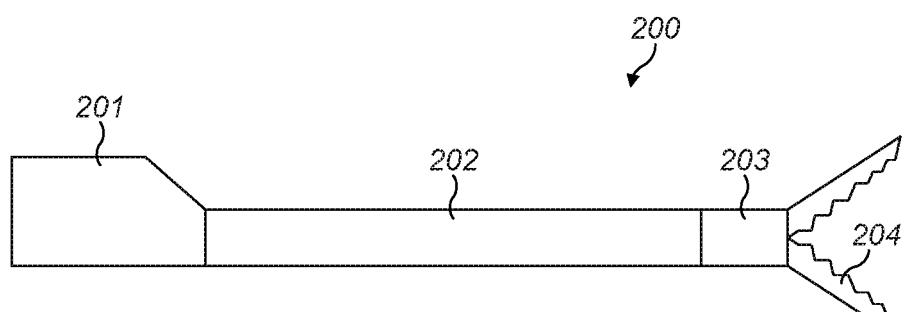
FIG. 2 illustrates a known surgical instrument.
Figure 3:
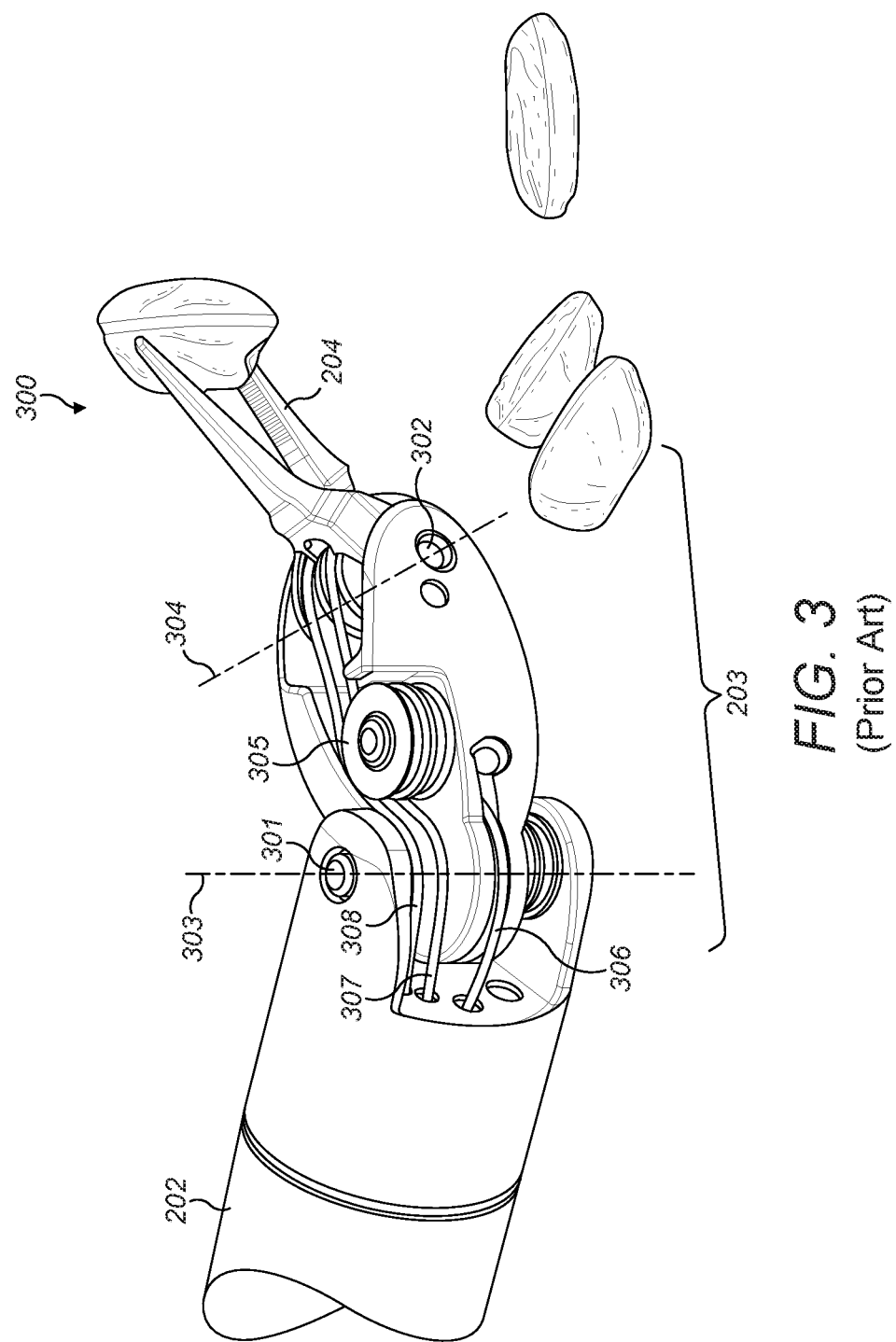
FIG. 3 illustrates a known arrangement of an articulated end effector of a surgical instrument.

The arm terminates in an attachment 405 for interfacing with the instrument 406. Suitably, the instrument 406 takes the form described with respect to FIG. 2. The instrument has a diameter less than 8 mm. Suitably, the instrument has a 5 mm diameter. The instrument may have a diameter which is less than 5 mm. The instrument diameter may be the diameter of the shaft. The instrument diameter may be the diameter of the profile of the articulation. Suitably, the diameter of the profile of the articulation matches or is narrower than the diameter of the shaft. The attachment 405 comprises a drive assembly for driving articulation of the instrument. Movable interface elements of the drive assembly interface mechanically engage corresponding movable interface elements of the instrument interface in order to transfer drive from the robot arm to the instrument. One instrument is exchanged for another several times during a typical operation. Thus, the instrument is attachable and detachable from the robot arm during the operation. Features of the drive assembly interface and the instrument interface aid their alignment when brought into engagement with each other, so as to reduce the accuracy with which they need to be aligned by the user.

The instrument 406 comprises an end effector for performing an operation. The end effector may take any suitable form. For example, the end effector may be smooth jaws, serrated jaws, a gripper, a pair of shears, a needle for suturing, a camera, a laser, a knife, a stapler, a cauteriser, a suctioner. As described with respect to FIG. 2, the instrument comprises an articulation between the instrument shaft and the end effector. The articulation comprises several joints which permit the end effector to move relative to the shaft of the instrument. The joints in the articulation are actuated by driving elements, such as cables. These driving elements are secured at the other end of the instrument shaft to the interface elements of the instrument interface. Thus, the robot arm transfers drive to the end effector as follows: movement of a drive assembly interface element moves an instrument interface element which moves a driving element which moves a joint of the articulation which moves the end effector.

Controllers for the motors, torque sensors and encoders are distributed with the robot arm. The controllers are connected via a communication bus to control unit 409. A control unit 409 comprises a processor 410 and a memory 411. Memory 411 stores in a non-transient way software that is executable by the processor to control the operation of the motors 407 to cause the arm 400 to operate in the manner described herein. In particular, the software can control the processor 410 to cause the motors (for example via distributed controllers) to drive in dependence on inputs from the sensors 408 and from a surgeon command interface 412. The control unit 409 is coupled to the motors 407 for driving them in accordance with outputs generated by execution of the software. The control unit 409 is coupled to the sensors 408 for receiving sensed input from the sensors, and to the command interface 412 for receiving input from it. The respective couplings may, for example, each be electrical or optical cables, or may be provided by a wireless connection. The command interface 412 comprises one or more input devices whereby a user can request motion of the end effector in a desired way. The input devices could, for example, be manually operable mechanical input devices such as control handles or joysticks, or contactless input devices such as optical gesture sensors. The software stored in memory 411 is configured to respond to those inputs and cause the joints of the arm and instrument to move accordingly, in compliance with a pre-determined control strategy. The control strategy may include safety features which moderate the motion of the arm and instrument in response to command inputs. Thus, in summary, a surgeon at the command interface 412 can control the instrument 406 to move in such a way as to perform a desired surgical procedure. The control unit 409 and/or the command interface 412 may be remote from the arm 400.

Figure 5A:
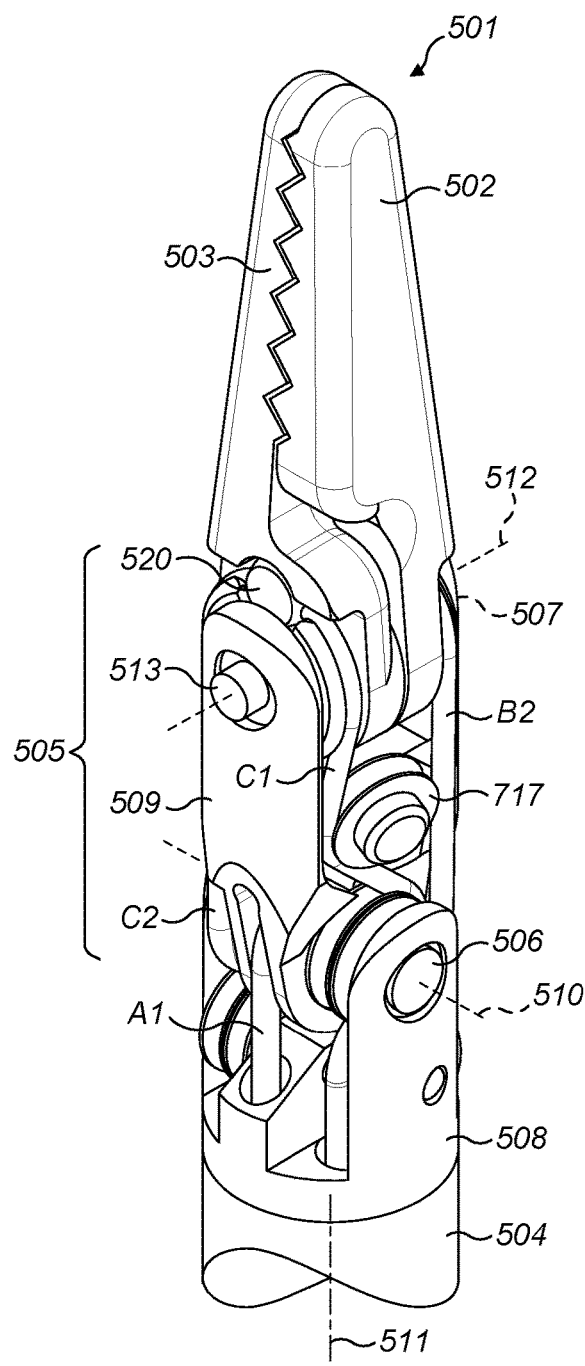
FIGS. 5a and 5b illustrate a distal end of a surgical instrument.
Figure 5B:
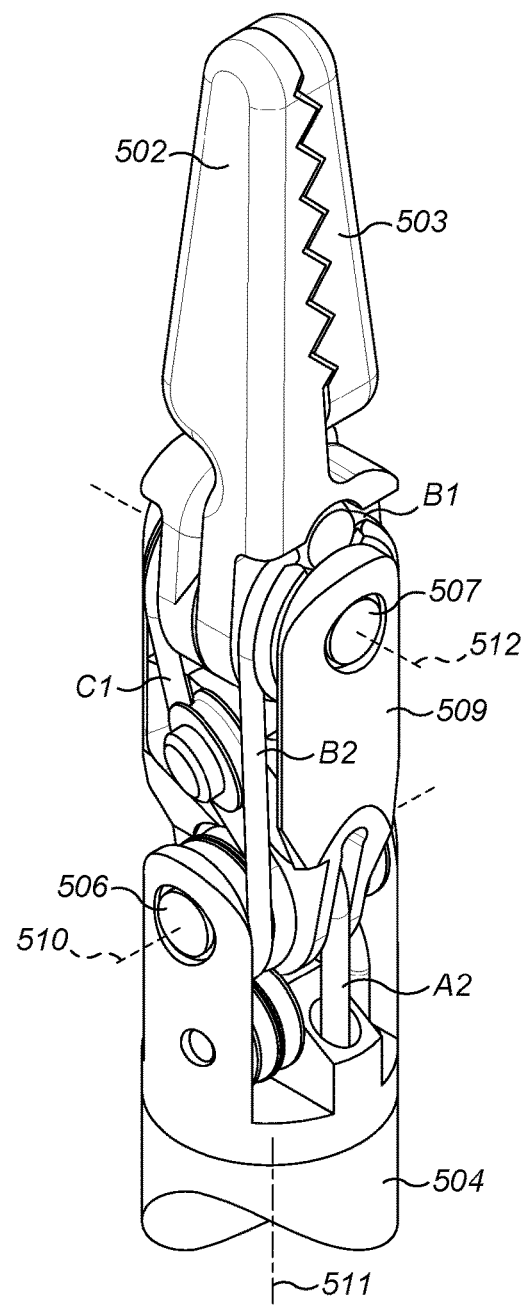

FIGS. 5a and 5b illustrate opposing views of the distal end of a surgical instrument. In FIGS. 5a and 5b, the end effector 501 comprises a pair of end effector elements 502, 503, which in FIGS. 5a and 5b are depicted as a pair of opposing serrated jaws. It will be understood that this is for illustrative purposes only. The end effector may take any suitably form, such as those described above. The end effector 501 is connected to the shaft 504 by articulation 505. Articulation 505 comprises joints which permit the end effector 501 to move relative to the shaft 504. A first joint 506 permits the end effector 501 to rotate about a first axis 510. The first axis 510 is transverse to the longitudinal axis of the shaft 511. A second joint 507 permits the first end effector element 502 to rotate about a second axis 512. The second axis 512 is transverse to the first axis 510. A third joint 513 permits the second end effector element 503 to rotate about the second axis 512. Suitably, the first end effector element 502 and the second end effector element 503 are independently rotatable about the second axis 512 by the second and third joints. The end effector elements may be rotated in the same direction or different directions by the second and third joints. The first end effector element 502 may be rotated about the second axis, whilst the second end effector element 503 is not rotated about the second axis. The second end effector element 503 may be rotated about the second axis, whilst the first end effector element 502 not rotated about the second axis.

Figure 9:
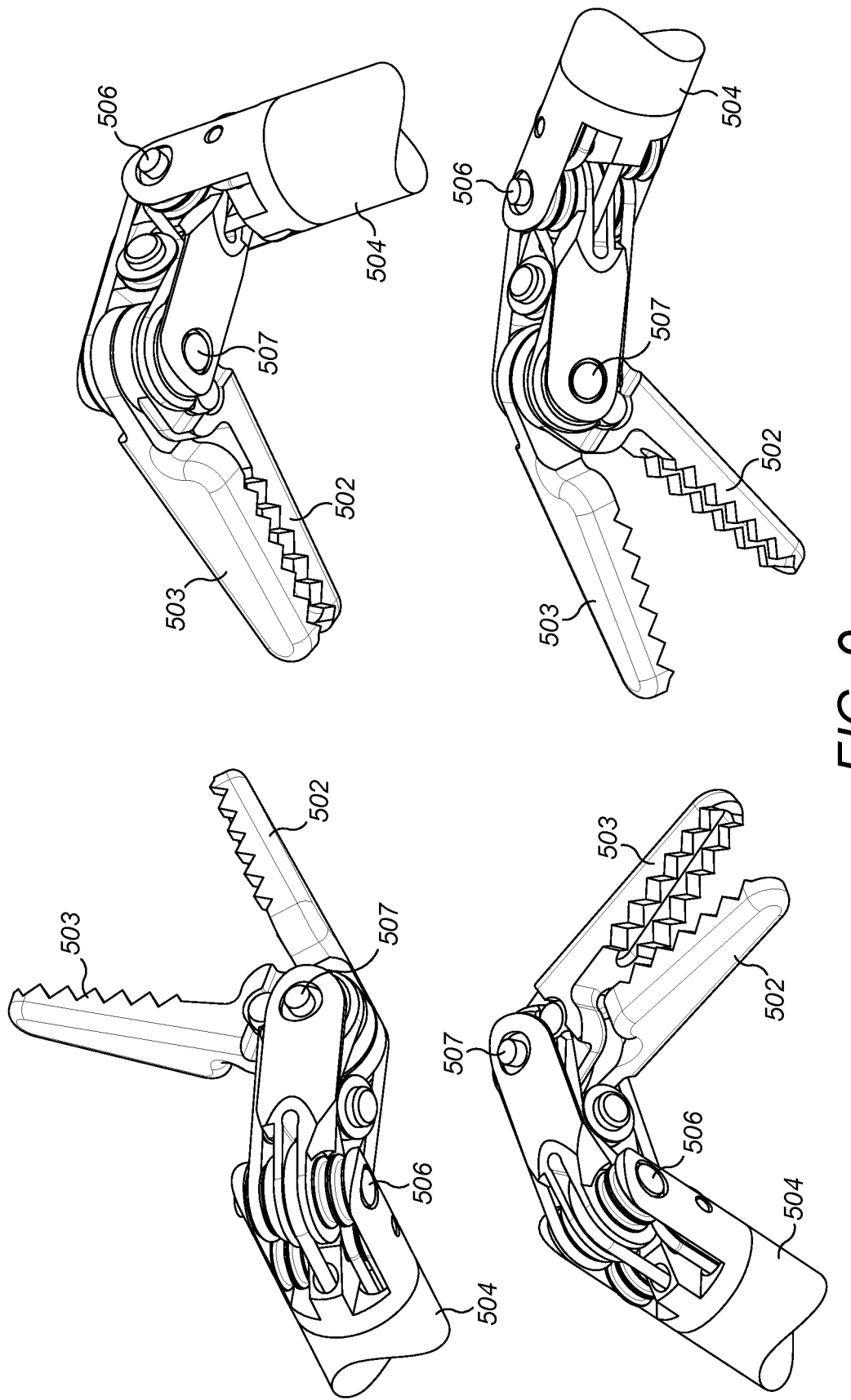
FIG. 9 illustrates non-straight configurations of the distal end of a surgical instrument.

FIGS. 5a and 5b depict a straight configuration of the surgical instrument in which the end effector is aligned with the shaft. In this orientation, the longitudinal axis of the shaft 511 is coincident with the longitudinal axis of the articulation and the longitudinal axis of the end effector. Articulation of the first, second and third joints enables the end effector to take a range of attitudes relative to the shaft. FIG. 9 illustrates some of the configurations of the distal end of the instrument in which articulation about all the first, second and third joints has been driven relative to the straight configuration of FIGS. 5a and 5b.

Returning to FIGS. 5a and 5b, the shaft terminates at its distal end in the first joint 506. The articulation 505 comprises a supporting body 509. At one end, the supporting body 509 is connected to the shaft 504 by the first joint 506. At its other end, the supporting body 509 is connected to the end effector 501 by second joint 507 and third joint 513. Thus, first joint 506 permits the supporting body 509 to rotate relative to the shaft 504 about the first axis 510; and the second joint 507 and third joint 513 permit the end effector elements 502, 503 to rotate relative to the supporting body 509 about the second axis 512.

In the figures, the second joint 507 and third joint 513 both permit rotation about the same axis 512. However, the second and third joints may alternatively permit rotation of the end effector elements about different axes. The axis of rotation of one of the end effector elements may be offset in the longitudinal direction of the shaft 504 from the axis of rotation of the other end effector element. The axis of rotation of one of the end effector elements may be offset in a direction transverse to the longitudinal direction of the shaft 504 from the axis of rotation of the other end effector element. The axis of rotation of one of the end effector elements may not be parallel to the axis of rotation of the other end effector element. The axes of rotation of the end effector elements 502, 503 may be offset in the longitudinal direction of the shaft and/or offset in a direction perpendicular to the longitudinal direction of the shaft and/or angled with respect to each other. This may be desirable as a result of the end effector elements being asymmetric. For example, in an electrosurgical element, a first end effector element may be powered and a second end effector element not powered and insulated from the first end effector element. To aid this, the axes of rotation of the two end effector elements may be offset in the direction perpendicular to the longitudinal direction of the shaft. In another example, a first end effector element may be a blade and a second end effector element a flat cutting surface. To aid use of the blade, the axes of rotation of the two end effector elements may be angled to one another.

The joints of the articulation are driven by driving elements. The driving elements are elongate elements which extend from the joints in the articulation through the shaft to the instrument interface. Suitably, each driving element can be flexed laterally to its main extent at least in those regions where it engages the internal components of the articulation and instrument interface. In other words, each driving element can be flexed transverse to its longitudinal axis in the specified regions. This flexibility enables the driving elements to wrap around the internal structure of the instrument, such as the joints and pulleys. The driving elements may be wholly flexible transverse to their longitudinal axes. The driving elements are not flexible along their main extents. The driving elements resist compression and tension forces applied along their length. In other words, the driving elements resist compression and tension forces acting in the direction of their longitudinal axes. The driving elements have a high modulus. The driving elements remain taut in operation. They are not permitted to become slack. Thus, the driving elements are able to transfer drive from the instrument interface to the joints. The driving elements may be cables.

Suitably, each joint is driven by a pair of driving elements. Referring to FIGS. 5a and 5b, the first joint 506 is driven by a first pair of driving elements A1,A2. The second joint 507 is driven by a second pair of driving elements B1,B2. The third joint is driven by a third pair of driving elements C1,C2. Suitably, each joint is driven by its own pair of driving elements. In other words, each joint is driven by a dedicated pair of driving elements. Suitably, the joints are independently driven. A pair of driving elements may be constructed as a single piece as shown for the third pair of driving elements in FIGS. 5a and 5b. In this case, the single piece is secured to the joint at one point. For example, the third pair of driving elements C1,C2 comprises a ball feature 520 which is secured to the third joint 513. This ensures that when the pair of driving elements is driven, the drive is transferred to motion of the joint about its axis. Alternatively, a pair of driving elements may be constructed as two pieces. In this case, each separate piece is secured to the joint.

The surgical instrument of FIGS. 5a and 5b further comprises a pulley arrangement around which the second and third pairs of driving elements are constrained to move. The pulley arrangement is better illustrated in FIGS. 6a and 6b. The supporting body 509 is not shown in FIGS. 6a and 6b in order to more clearly illustrate the pulley arrangement. The pulley arrangement comprises a first set of pulleys 601. The first set of pulleys 601 is rotatable about the first axis 510. Thus, the first set of pulleys 601 rotate about the same axis as the first joint 506. The pulley arrangement further comprises a second set of pulleys 602. The pulley arrangement further comprises a pair of redirecting pulleys 603.

Figure 7:
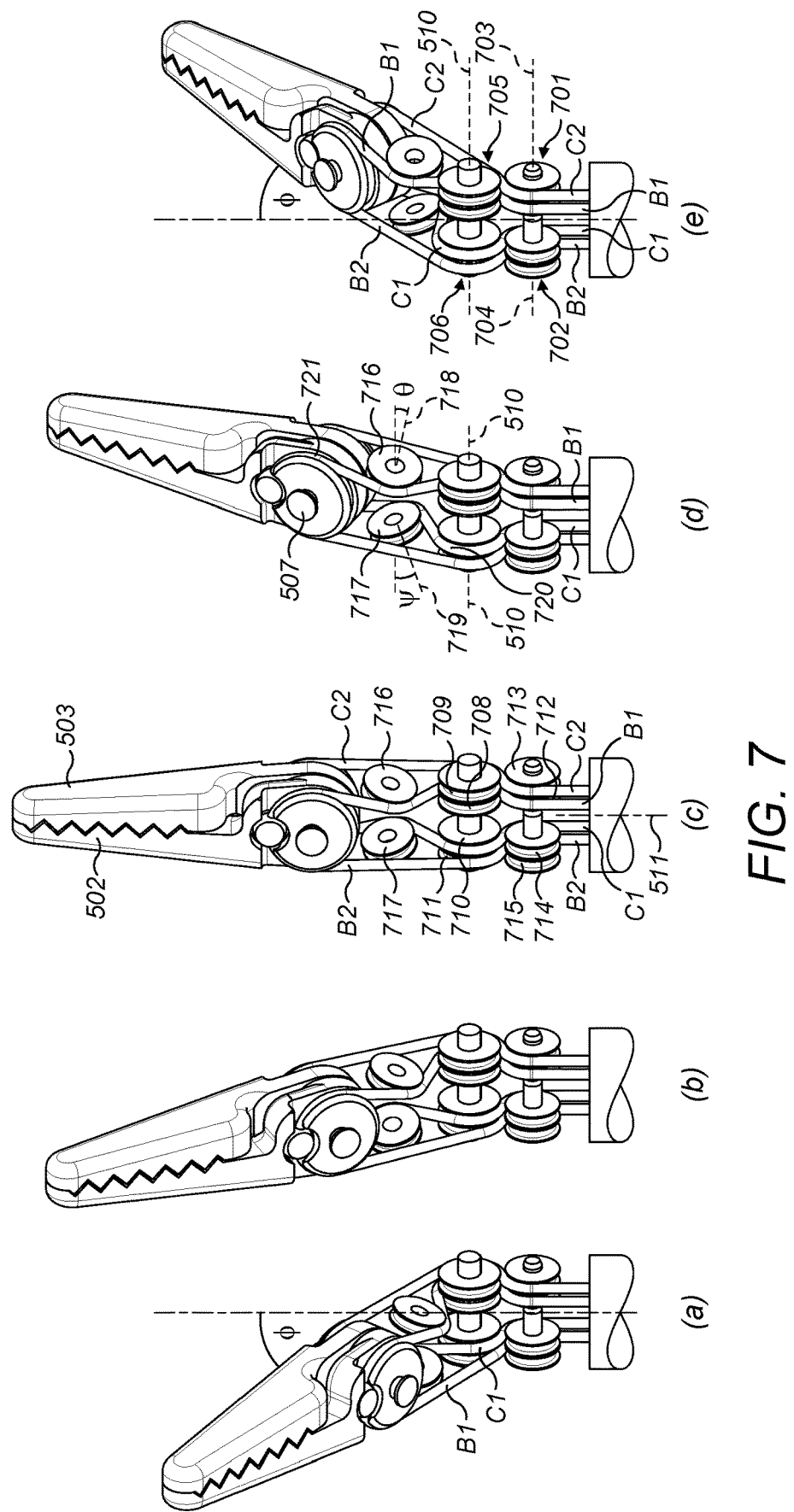
FIG. 7 illustrates a pulley arrangement of the distal end of the surgical instrument of FIGS. 5a and 5b in a variety of non-straight configurations.

The pulley arrangement is more clearly illustrated in FIG. 7. The supporting body, the first joint and the first pair of driving elements have all been omitted from FIG. 7 in order to more clearly illustrate the pulley arrangement. The second set of pulleys comprises a first pulley 701 and a second pulley 702. The first pulley 701 is rotatable about a third axis 703 which is parallel to the first axis 510. The third axis 703 is offset from the first axis 510 both in the longitudinal direction of the shaft and also transverse to the longitudinal direction of the shaft. The second pulley 702 is rotatable about a fourth axis 704 which is parallel to the first axis 510.

Figure 6A:
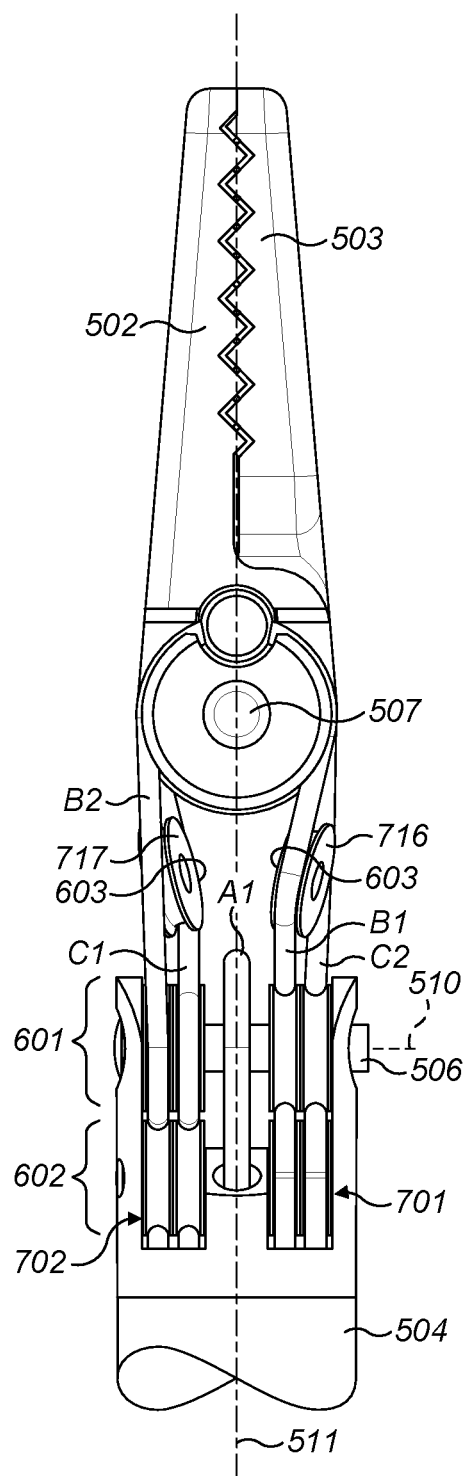
FIGS. 6a and 6b illustrate a pulley arrangement of the distal end of the surgical instrument of FIGS. 5a and 5b in a straight configuration.
Figure 6B:
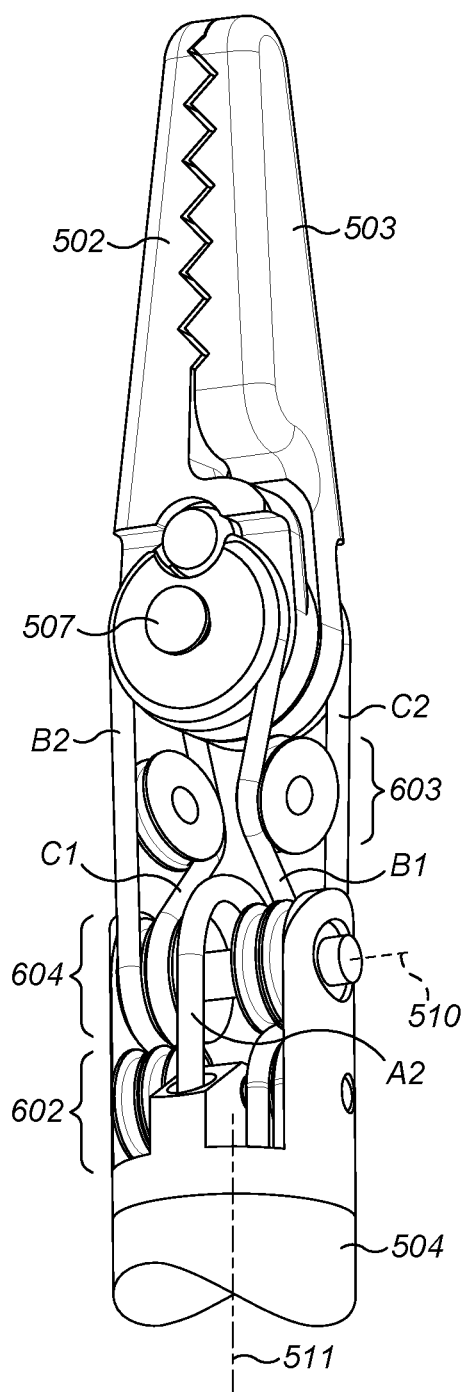
Figure 8:
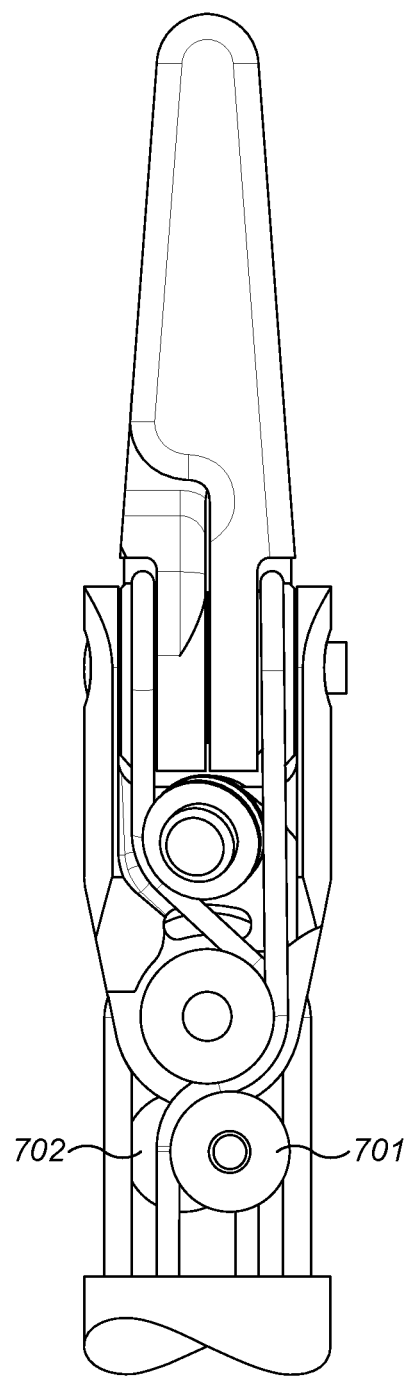
FIG. 8 illustrates the offset pulleys of the pulley arrangement shown in FIGS. 5a and 5b.

The fourth axis 704 is offset from the first axis 510 both in the longitudinal direction of the shaft and also transverse to the longitudinal direction of the shaft. The third and fourth axes are parallel but offset from each other. The third axis 703 and fourth axis 704 are in the same plane perpendicular to the longitudinal direction of the shaft. FIG. 8 illustrates the distal end of the surgical instrument from a different view which more clearly shows the offset axes of the first pulley 701 and the second pulley 702 of the second set of pulleys. By offsetting the first pulley 701 and the second pulley 702, the driving element wrapped around each pulley is able to extend down the shaft after having wrapped around the pulley. As shown in FIG. 6a, the first pulley 701 and second pulley 702 of the second set of pulleys 602 are located on opposing sides of the first joint 506 in a longitudinal direction of the shaft 504. The first pulley 701 and second pulley 702 are located on opposing sides of the first pair of driving elements A1,A2.

The second set of pulleys is located between the first set of pulleys and the instrument interface end of the shaft. Suitably, the second set of pulleys is located within the shaft as shown in the figures. Alternatively, the second set of pulleys may be located within the articulation between the first joint 506 and the second joint 507. However, by locating the second set of pulleys at the distal end of the shaft 508, the distance between the first and second joints is reduced compared to the alternative arrangement in which the second set of pulleys are located in the articulation, thereby reducing the stiffness of the supporting body 509 required to maintain accurate positioning of the end effector 501.

The first set of pulleys 601 comprises a first pulley 705 and a second pulley 706. Both the first pulley 705 and the second pulley 706 rotate about the first axis 510. The first pulley 705 and the second pulley 706 of the first set of pulleys are located on opposing sides of the first joint 506 in a longitudinal direction of the shaft 504. The first pulley 705 and the second pulley 06 are located on opposing ends of the first axis 510. The first pulley 705 and the second pulley 706 are located on opposing sides of the first pair of driving elements A1,A2.

The second pair of driving elements B1,B2 is constrained to move around opposing sides of the first pulley 705 and the second pulley 706 of the first set of pulleys 601. The second pair of driving elements B1,B2 is constrained to move around opposing sides of the first pulley 701 and the second pulley 702 of the second set of pulleys 601. The second pair of driving elements is constrained to move around opposing sides of the first pulley 705 of the first set of pulleys 601 and the first pulley 701 of the second set of pulleys 602. The second pair of driving elements is constrained to move around opposing sides of the second pulley 706 of the first set of pulleys 601 and the second pulley 702 of the second set of pulleys 602.

The third pair of driving elements C1,C2 is constrained to move around opposing sides of the first pulley 705 and the second pulley 706 of the first set of pulleys 601. The third pair of driving elements C1,C2 is constrained to move around opposing sides of the first pulley 701 and the second pulley 702 of the second set of pulleys 601. The third pair of driving elements is constrained to move around opposing sides of the first pulley 705 of the first set of pulleys 601 and the first pulley 701 of the second set of pulleys 602. The third pair of driving elements is constrained to move around opposing sides of the second pulley 706 of the first set of pulleys 601 and the second pulley 702 of the second set of pulleys 602.

The second and third pairs of driving elements are each constrained to extend over the first joint 506 in order to reach the second and third joints respectively. Thus, the first one of the second pair of driving elements B1 passes over one side of the first pulley 705 of the first set of pulleys on the first joint axis 510, and the second one of the second pair of driving elements B2 passes over an opposing side of the second pulley 706 of the first set of pulleys on the first joint axis 510, so that whatever rotation there is of the supporting body 509 about the first joint 506, the length of the second pair of driving elements B1,B2 is maintained the same. Similarly, the first one of the third pair of driving elements C1 passes over one side of the second pulley 706 of the first set of pulleys on the first joint axis 510, and the second one of the third pair of driving elements C2 passes over an opposing side of the first pulley 705 of the first set of pulleys on the first joint axis 510, so that whatever rotation there is of the supporting body 509 about the first joint 506, the length of the third pair of driving elements C1,C2 is maintained the same. If the arrangement of the instrument interface is symmetric for both the second pair of driving elements B1,B2 and the third pair of driving elements C1,C2, then the length of the second pair of driving elements is the same as the length of the third pair of driving elements for all rotation angles of the supporting body 509 about the first joint 506. In every configuration of the surgical instrument, the second pair of driving elements and the third pair of driving elements remain taut. They are never slack. Thus, there is no backlash when articulating any of the joints of the surgical instrument. Thus, full control of all three degrees of freedom of movement of the surgical instrument is achieved in every configuration of the surgical instrument.

Suitably, each pulley of the first set of pulleys 601 comprises a pair of pulley elements. The first pulley 705 comprises an inside pulley element 708 and an outside pulley element 709. Inside pulley element 708 is located between the outside pulley element 709 and the first pair of driving elements A1,A2. Suitably, inside pulley element 708 abuts outside pulley element 709. The inside pulley element 708 may be fast with the outside pulley element 709. The inside pulley element 708 may be integrally formed with the outside pulley element 709. The second pulley 706 comprises an inside pulley element 710 and an outside pulley element 711. Inside pulley element 710 is located between the outside pulley element 711 and the first pair of driving element A1,A2. Suitably, inside pulley element 710 abuts outside pulley element 711. The inside pulley element 710 may be fast with the outside pulley element 711. The inside pulley element 710 may be integrally formed with the outside pulley element 711. Each pulley element comprises a groove for seating a driving element.

Suitably, each pulley of the second set of pulleys 602 comprises a pair of pulley elements. The first pulley 701 comprises an inside pulley element 712 and an outside pulley element 713. Inside pulley element 712 is located between the outside pulley element 713 and the first pair of driving elements A1,A2. Suitably, inside pulley element 712 abuts outside pulley element 713. The inside pulley element 712 may be fast with the outside pulley element 713. The inside pulley element 712 may be integrally formed with the outside pulley element 713. The second pulley 702 comprises an inside pulley element 714 and an outside pulley element 715. Inside pulley element 714 is located between the outside pulley element 715 and the first pair of driving element A1,A2. Suitably, inside pulley element 714 abuts outside pulley element 715. The inside pulley element 714 may be fast with the outside pulley element 715. The inside pulley element 714 may be integrally formed with the outside pulley element 715. Each pulley element comprises a groove for seating a driving element.

The second pair of driving elements B1,B2 is constrained to move around the inside pulley element 712 of the first pulley of the second set of pulleys and the outside pulley element 715 of the second pulley of the second set of pulleys. The second pair of driving elements B1, B2 is constrained to move around the inside pulley element 708 of the first pulley of the first set of pulleys and the outside pulley element 711 of the second pulley of the first set of pulleys.

The third pair of driving elements C1,C2 is constrained to move around the outside pulley element 713 of the first pulley of the second set of pulleys and the inside pulley element 714 of the second pulley of the second set of pulleys. The third pair of driving elements C1,C2 is constrained to move around the outside pulley element 709 of the first pulley of the first set of pulleys and the inside pulley element 710 of the second pulley of the first set of pulleys.

Thus, the second pair of driving elements B1,B2 has a symmetrically opposing path around the first and second sets of pulleys 601, 602 than the third pair of driving elements C1,C2. In the straight configuration of the instrument in which the end effector is aligned with the shaft, the path of the second pair of driving elements B1,B2 about the pulley arrangement is rotationally symmetrical about the longitudinal axis of the shaft 511 to the path of the third pair of driving elements C1,C2 about the pulley arrangement. The second and third pairs of driving elements B1,B2 and C1,C2 emerge from the second set of pulleys 602 into the distal end of the shaft in a symmetrical arrangement. As can be more easily seen on FIG. 7, the driving elements B1 and C2 emerge adjacent to each other on one side of the shaft, and the driving elements C1 and B2 emerge adjacent to each other on an opposing side of the shaft. The arrangement of driving elements B1 and C2 in the shaft is rotationally symmetrical to the arrangement of driving elements C1 and B2 in the shaft, about the longitudinal axis of the shaft 511. The second set of pulleys 602 redirects the second and third pairs of driving elements from the first set of pulleys 601 into the shaft in this manner.

FIG. 7 illustrates the distal end of the surgical instrument in five different configurations. Configuration (c) is the straight configuration previously mentioned, in which the end effector is aligned with the instrument shaft. In configurations (a), (b), (d) and (e), rotation about the first joint has occurred relative to configuration (c). In configurations (a), (b), (d) and (e), no rotation about either the second or third joint has occurred relative to configuration (c). Starting from configuration (c), the driving element A2 (not shown) is pulled in order to cause the rotation about the first axis 510 leading to the arrangement of configuration (b). The driving element A2 is further pulled to cause further rotation about the first axis 510 to lead to the arrangement of configuration (a). Starting from configuration (c), the driving element A1 (not shown) is pulled in order to cause rotation about the first axis 510 in an opposing direction to that in configurations (a) and (b), thereby leading to the arrangement of configuration (d). The driving element A1 is further pulled to cause further rotation about the first axis 510 to lead to the arrangement of configuration (e).

Rotation of the end effector 501 about the first axis 510 is bounded by the maximum travel of the first pair of driving elements A1,A2 about the first joint 506. Configuration (a) shows the end effector 501 at maximum rotation about the first axis 510 in one direction, and configuration (e) shows the end effector 501 at maximum rotation about the first axis 510 in the opposing direction. The maximum rotation angle relative to the longitudinal axis of the shaft 511 in both configurations is the angle 4. The second set of pulleys 602 are located relative to the first set of pulleys 601 so as to ensure that the second and third pairs of driving elements are retained in contact with both the first set of pulleys 601 and the second set of pulleys 602 even at the maximum rotation angle 4. For all rotation angles of the end effector 501 about the first axis 510, the end effector 501 always lies within the cone defined by the tangential line connecting the first pulley 701 of the second set of pulleys and the first pulley 705 of the first set of pulleys. That tangential line is the path taken by the driving element. The end effector 501 lies in this cone when the second and third joints are retained in the straight configurations of FIGS. 5a and 5b, as shown in all the configurations of FIG. 7. As can be seen from FIG. 7, without the second set of pulleys 602, the driving elements B2 and C1 would lose contact with the first set of pulleys 601 in configuration (a). Without the second set of pulleys 602, the driving elements B1 and C2 would lose contact with the first set of pulleys 601 in configuration (e).

The second and third pairs of driving elements are retained in contact with the first and second sets of pulleys for all rotation angles of the end effector relative to the longitudinal axis of the shaft. Thus, regardless of the rotation about the first joint 506, the length of the second pair of driving elements B1,B2 will be maintained the same. Also, regardless of the rotation about the first joint 506, the length of the third pair of driving elements C1,C2 will be maintained the same. Thus, the second set of pulleys enable tension to be retained in the second and third driving elements regardless of how the first joint 506 is driven about the first axis 510. Thus, control of the second and third driving elements is retained regardless of how the first joint 506 is driven about the first axis 510.

The pulley arrangement further comprises a pair of redirecting pulleys 716,717. These redirecting pulleys are in the articulation 505 between the first joint 506 and the second and third joints 507, 513. The redirecting pulleys are positioned so as to redirect the second pair of driving elements B1,B2 from the first set of pulleys 601 to the second joint 507 and to redirect the third pair of driving elements C1,C2 from the first set of pulleys 601 to the third joint 513.

The second pair of driving elements B1,B2 is constrained to move around the first redirecting pulley 716. The first redirecting pulley 716 rotates about a first redirecting pulley axis 718. The first redirecting pulley axis 718 is at an angle $\vartheta$ to the first axis 510. The angle $\vartheta$ is such that the first one of the second pair of driving elements B1 is redirected from a take-off point of the first pulley 705 of the first set of pulleys 601 to a pick-up point 721 on the second joint 507. Suitably, the first redirecting pulley 716 comprises a groove which seats the driving element B1. The third pair of driving elements C1,C2 is not constrained to move around the first redirecting pulley 716. However, the second one of the third pair of driving elements C2 does pass by the first redirecting pulley 716 between its take-off point of the third joint 513 and its pick-up point on the first pulley 705 of the first set of pulleys 601. The driving element C2 may be partially enclosed by the first redirecting pulley 716. For example, the driving element C2 may partially pass between the wings of the groove of the first redirecting pulley 716, but the driving element C2 is not seated in the groove of the first redirecting pulley 716.

The third pair of driving elements C1,C2 is constrained to move around the second redirecting pulley 717. The second redirecting pulley 717 rotates about a second redirecting pulley axis 719. The second redirecting pulley axis 719 is at an angle ψ to the first axis 510. The angle ψ is such that the first one of the third pair of driving elements C1 is redirected from a take-off point 720 of the second pulley 706 of the first set of pulleys 601 to a pick-up point on the third joint 513. Suitably, the second redirecting pulley 717 comprises a groove which seats the driving element C1. The second pair of driving elements B1,B2 is not constrained to move around the second redirecting pulley 717. However, the second one of the second pair of driving elements B2 does pass by the second redirecting pulley 717 between its take-off point 720 of the second joint 507 and its pick-up point on the second pulley 706 of the first set of pulleys 601. The driving element B2 may be partially enclosed by the second redirecting pulley 717. For example, the driving element B2 may partially pass between the wings of the groove of the second redirecting pulley 717, but the driving element B2 is not seated in the groove of the second redirecting pulley 717.

A take-off point is the point at which a driving element loses contact with a pulley. A pick-up point is the point at which a driving element first contacts a pulley. For a driving element passing directly from a first pulley to a second pulley, the take-off point of the driving element from the first pulley and the pick-up point of the driving element on the second pulley are points on a line which is tangential to both the first pulley and the second pulley, the take-off point being where that tangential line intersects the first pulley, and the pick-up point being where that tangential line intersects the second pulley. This is for the purposes of explanation only and treats as negligible the thickness of the driving element. Thus, in reality, the tangential line has a thickness equal to the thickness of the driving element, with the take-off point being where one side of the tangential line meets the first pulley, and the pick-up point being where the other side of the tangential line meets the second pulley.

The redirecting pulley 716 causes the driving element B1 to wrap more fully around the second joint 507 than would happen if the redirecting pulley 716 was not there, thereby increasing the length of engagement between the driving element B1 and the second joint 507. Thus, the driving element B1 has a greater travel around the second joint 507, and is hence able to cause a larger rotation of the end effector element 502 about the second axis 512 than would be possible without the redirecting pulley 716. The redirecting pulley 716 causes the pick-up point of the driving element B1 on the second joint 507 to change relative to where it would have been without the redirecting pulley 716.

The redirecting pulley 717 causes the driving element C1 to wrap more fully around the third joint 513 than would happen if the redirecting pulley 717 was not there, thereby increasing the length of engagement between the driving element C1 and the third joint 513. Thus, the driving element C1 has a greater travel around the third joint 513, and is hence able to cause a larger rotation of the end effector element 503 about the second axis 512 than would be possible without the redirecting pulley 717. The redirecting pulley 717 causes the pick-up point of the driving element C1 on the third joint 513 to change relative to where it would have been without the redirecting pulley 717.

The redirecting pulleys are each located towards the outside edge of the articulation, on opposing sides of the articulation. This is more easily seen on FIG. 5a. As seen in FIG. 6a, each redirecting pulley is located between the longitudinal axis of the articulation and the external profile of the articulation, on opposing sides of the articulation. Suitably, the diameter of each redirecting pulley is maximised for the space available. In other words, the redirecting pulley is as large as possible, whilst enabling one driving element to engage the pulley on one side of the pulley and another driving element to pass next to the pulley on the opposing side of the pulley without snagging, the pulley and the two driving elements being encapsulated within the profile of the articulation.

The first redirecting pulley 716 is located in a plane defined by the following three points: (i) the desired take-off point of driving element B1 from the first pulley 705 of the first set of pulleys 601, (ii) the desired pick-up point of driving element B1 on the second joint 507, and (iii) a point on the boundary of the articulation, the point being such that the first redirecting pulley 716 is encapsulated within the boundary of the articulation when located in the plane. Suitably, the first redirecting pulley 716 is as large as possible whilst still being located in this plane, encapsulated within the profile of the articulation, not impeding the path of the driving element C2, and enabling driving element B1 to freely move around it.

The second redirecting pulley 717 is located in a plane defined by the following three points: (i) the desired take-off point of driving element C1 from the second pulley 706 of the first set of pulleys 601, (ii) the desired pick-up point of driving element C1 on the third joint 513, and (iii) a point on the boundary of the articulation, the point being such that the second redirecting pulley 717 is encapsulated within the boundary of the articulation when located in the plane. Suitably, the second redirecting pulley 717 is as large as possible whilst still being located in this plane, encapsulated within the profile of the articulation, not impeding the path of the driving element B2, and enabling driving element C1 to freely move around it.

The desired take-off points and pick-up points are determined so as to allow the desired travel of the driving elements around the second and third joints so as to allow the desired maximum rotation of the end effector elements about the second axis.

The first and second redirecting pulleys are located in different planes. As can be seen in FIG. 6a, those planes may be symmetrical about a plane which is perpendicular to the first axis 510. Those planes may be rotationally symmetrical about a plane which is perpendicular to the first axis 510. Specifically, those planes may be rotationally symmetrical about a line in a plane which is perpendicular to the first axis 510. When the instrument is in the straight configuration illustrated in FIG. 6a, those planes are rotationally symmetrical about the longitudinal axis of the shaft 511. This is second order rotational symmetry. Those planes may be a reflection of each other in the plane which is perpendicular to the first axis 510. In the example illustrated, the end effector elements 502 and 503 are rotationally symmetrical, and the paths of the driving elements about the joints 507 and 513 are rotationally symmetrical. Alternatively, the axes of the end effector elements 502 and 503 may be rotationally asymmetrical and/or the paths of the driving elements about the joints 507 and 513 may be asymmetrical. The paths of the driving elements about the joints 507 and 513 may be asymmetrical as a result of the joints having different diameters (to enable different tension ratios) and/or being positioned at different offsets from the centreline of the supporting body 509. In any of these alternative examples, the first and second redirecting pulleys 716 and 717 would not be rotationally symmetric. They would have different sizes and/or different positions in order to cause the driving elements to have the desired take-off points and pick-up points as previously described.

Suitably, the whole pulley arrangement comprising the first set of pulleys, the second set of pulleys and the redirecting pulleys is symmetrical about a plane which is perpendicular to the first axis 510. Specifically, a first partial arrangement comprising the first pulley of the first set of pulleys 705, the first pulley of the second set of pulleys 701, and the first redirecting pulley 716 is rotationally symmetrical to a second partial arrangement comprising the second pulley of the first set of pulleys 706, the second pulley of the second set of pulleys 702, and the second redirecting pulley 717 about a plane which is perpendicular to the first axis 510. Suitably, the first partial arrangement is a reflection of the second partial arrangement in the mentioned plane which is perpendicular to the first axis 510. The second pair of driving elements B1,B2 is constrained to move around the pulley arrangement in a rotationally symmetrically opposing manner to that in which the third pair of driving elements C1,C2 is constrained to move around the pulley arrangement. Since the pulley arrangement has the described symmetry, the second and third driving elements that are constrained to move symmetrically around the pulley arrangement also have the same symmetry. Thus, the path of the second pair of driving elements B1,B2 about the pulley arrangement is rotationally symmetrical to the path of the third pair of driving elements C1,C2 about the pulley arrangement.

Figure 10:
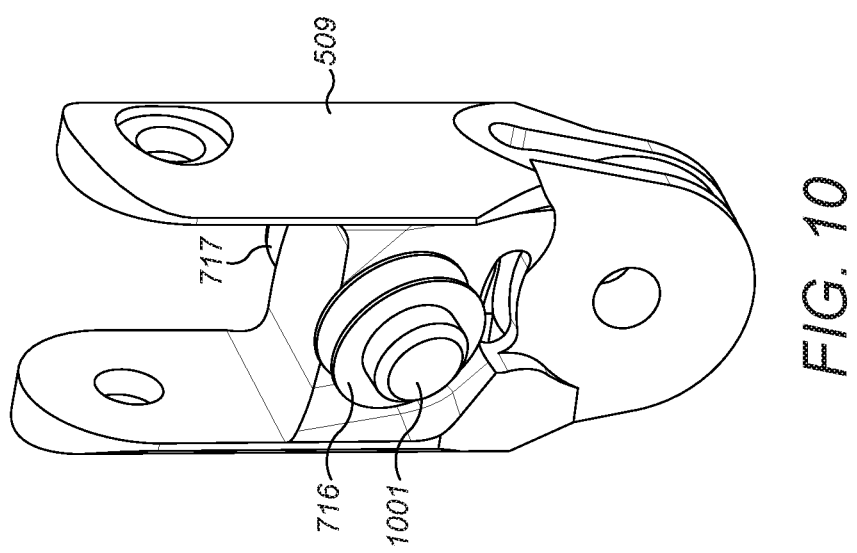
FIG. 10 illustrates a supporting body and redirecting pulleys of the articulation of a surgical instrument.

In an exemplary implementation, the first and second redirecting pulleys are mounted on the supporting body 509. FIG. 10 illustrates the supporting body 509 and the redirecting pulleys in isolation. Each redirecting pulley is mounted to a surface of the supporting body 509 by a spindle. The spindle 1001 secures the first redirecting pulley 716 to the supporting body 509. A spindle 1103 also secures the second redirecting pulley 717 to the supporting body 509.

Figure 11:
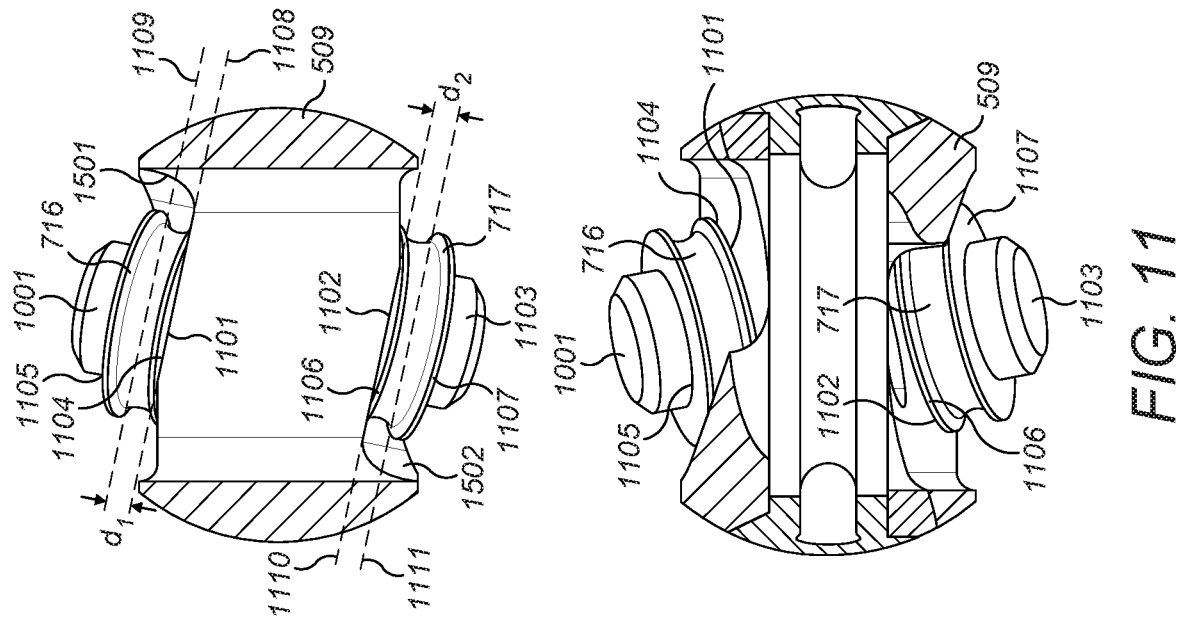
FIG. 11 illustrates a different view of the supporting body and redirecting pulleys of FIG. 10.

As is more clearly illustrated in the view shown in FIG. 11, the supporting body 509 has a bevelled surface 1101 onto which the first redirecting pulley 716 is mounted. The first redirecting pulley 716 has a mounting surface 1104 which faces the bevelled surface 1101 of the supporting body 509. The mounting surface 1104 is flush with the bevelled surface 1101.

The first redirecting pulley has an opposing surface 1105 which opposes the mounting surface 1104. The opposing surface 1105 is parallel to the mounting surface 1104. The supporting body 509 has a further bevelled surface onto which the second redirecting pulley 717 is mounted by spindle 1103. The second redirecting pulley 717 has a mounting surface 1106 which faces the bevelled surface 1102 of the supporting body 509. The mounting surface 1106 is flush with the bevelled surface 1102. The second redirecting pulley has an opposing surface 1107 which opposes the mounting surface 1102. The opposing surface 1107 is parallel to the mounting surface 1102.

The bevelled surfaces of the supporting body 509 are not parallel to the longitudinal axis of the supporting body. The bevelled surface 1101 of the supporting body 509 is located in a plane 1108 parallel to the plane 1109 in which the first redirecting pulley 716 is located. In other words, the bevelled surface 1101 is located in a plane 1108 parallel to the plane 1109 defined by the following three points: (i) the desired take-off point of driving element B1 from the first pulley 705 of the first set of pulleys 601, (ii) the desired pick-up point of driving element B1 on the second joint 507, and (iii) a point on the boundary of the articulation, the point being such that the first redirecting pulley 716 is encapsulated within the boundary of the articulation when located in the plane 1109. The plane 1108 of the bevelled surface 1101 is offset from the plane 1109 defined by these points by half the width of the first redirecting pulley 716, illustrated as $d_1$ in FIG. 11.

The bevelled surface 1102 of the supporting body 509 is located in a plane 1110 parallel to the plane 1111 in which the second redirecting pulley 717 is located. In other words, the bevelled surface 1102 is located in a plane 1110 parallel to the plane 1111 defined by the following three points: (i) the desired take-off point of driving element C1 from the second pulley 706 of the first set of pulleys 601, (ii) the desired pick-up point of driving element C1 on the third joint 513, and (iii) a point on the boundary of the articulation, the point being such that the second redirecting pulley 717 is encapsulated within the boundary of the articulation when located in the plane 1111. The plane 1110 of the bevelled surface 1101 is offset from the plane 1111 defined by these points by half the width of the second redirecting pulley 717, illustrated as $d_2$ in FIG. 11. Suitably, the first redirecting pulley 716 and the second redirecting pulley 717 are the same shape and size. In this case, $d_1=d_2$.

Figure 13:
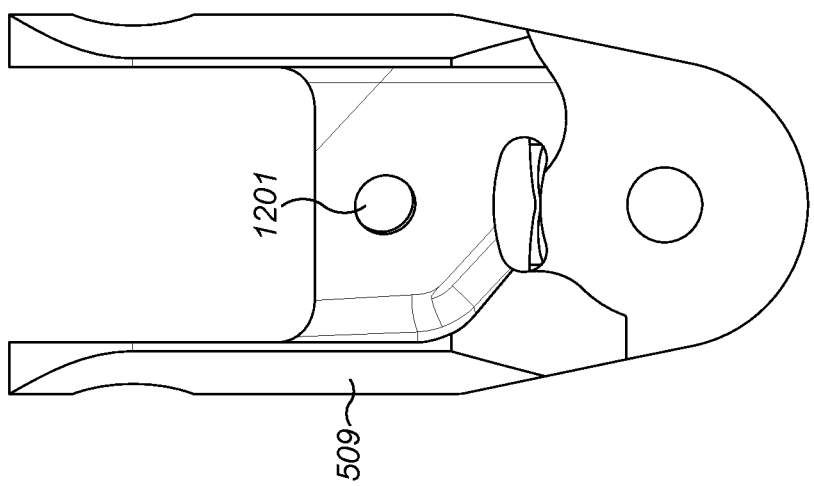
FIGS. 12 and 13 illustrate the supporting body of the articulation of FIGS. 10 and 11 in isolation.
Figure 12:
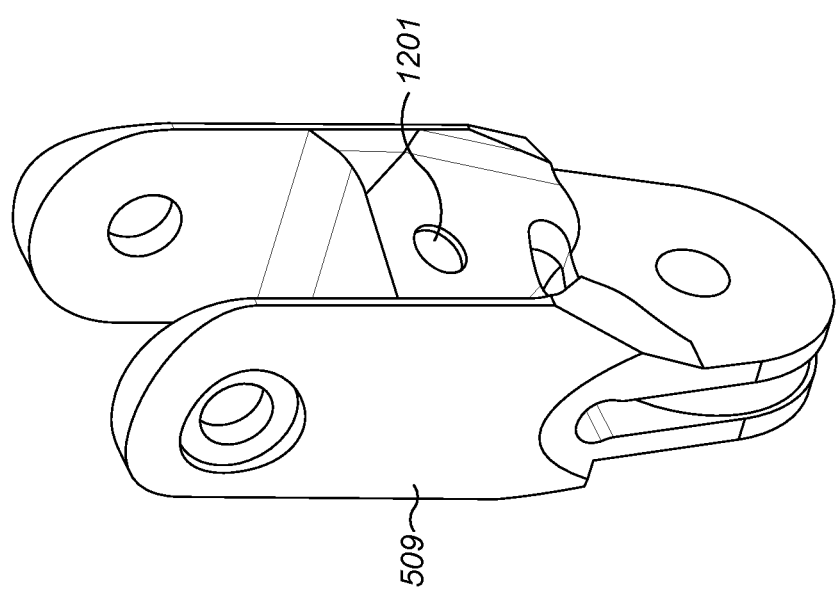

As discussed above, each redirecting pulley is mounted to the corresponding bevelled surface of the supporting body by a spindle. The spindle comprises a spindle body and a spindle head. The spindle body passes through a central aperture of the redirecting pulley. The central aperture is a through-hole which extends perpendicularly between the mounting surface and the opposing surface of the redirecting pulley. The spindle body passes through the central aperture of the redirecting pulley into a bore of the supporting body. FIGS. 12 and 13 illustrate the supporting body 509 in isolation. An exemplary implementation of the bore of the supporting body is depicted in these figures. The bore is a recess in the supporting body which tapers to a point. The spindle body passes through the initial opening of the bore and securely lodges in the tapered section. The spindle head is bigger than the central aperture of the redirecting pulley, and thus is unable to pass through the central aperture of the redirecting pulley. Consequently, the spindle head secures the redirecting pulley flush against the bevelled surface of the supporting body. The spindle head contacts at least a portion of the opposing surface of the redirecting pulley, through which contact the redirecting pulley is retained against the bevelled surface.

Figure 14:
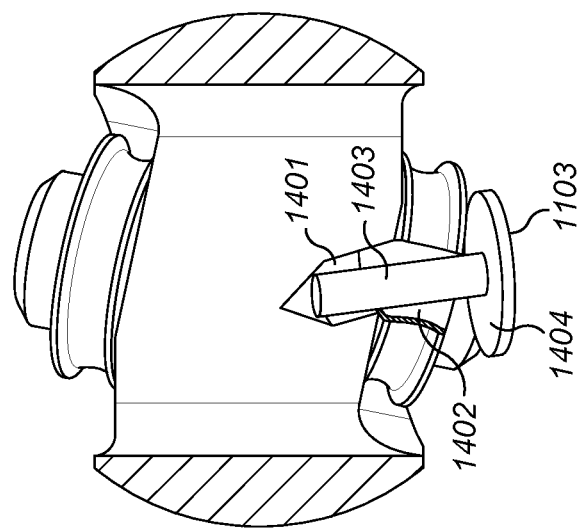
FIG. 14 illustrates a spindle mounted redirecting pulley mounted to the supporting body of FIGS. 12 and 13.

Referring to FIG. 14, the diameter of the bore 1401 through the supporting body is greater than the diameter of the spindle body 1403. The diameter of the central aperture 1402 of the redirecting pulley may be greater than the diameter of the spindle body 1403. Thus, the spindle body may loosely fit through the central aperture of the redirecting pulley. The spindle body loosely fits through the bore of the supporting body except for in the region in which it is secured to the bore, in the example above the tapered section. Typically, the bore through the supporting body is created by drilling through the bevelled surface of the supporting body during manufacture. Since the opening of the bore in the bevelled surface has a greater diameter than the spindle body, the precision of the angle at which the supporting body is drilled to create the bore is not critical. The spindle sits in the bore at the correct angle for the redirecting pulley to sit flush with the bevelled surface. It would have been critical that the angle of the bore was drilled very accurately if the fit of the spindle body through the bore was a tight fit and was the means by which the redirecting pulley was caused to rotate about the redirecting pulley axis 718,719. In that case the pulley would have been mounted tight on to the spindle which would have been mounted tight into the bore to stop the pulley from precessing. Thus, there would have been no room for manufacturing deviations in the angle at which the hole was drilled through the supporting body. In the described implementation, however, the redirecting pulley is caused to rotate about the redirecting pulley axis 718,719 as a result of the redirecting pulley being held flush against a bevelled surface of the supporting body 509 which is perpendicular to the redirecting pulley axis 718,719. Thus, greater manufacturing variation in the accuracy of the angle at which the bore is drilled through the supporting body is acceptable in the described implementation.

The bevelled surfaces 1101 and 1102 of the supporting body are not parallel to each other. The bevelled surfaces may be symmetrical about a plane which is perpendicular to the first axis 510. The bevelled surfaces may be rotationally symmetrical about a plane which is perpendicular to the first axis 510. Specifically, the bevelled surfaces may be rotationally symmetrical about a line in a plane which is perpendicular to the first axis 510. When the instrument is in the straight configuration illustrated in FIG. 5a, the bevelled surfaces are rotationally symmetrical about the longitudinal axis of the shaft 511. This is second order rotational symmetry. The bevelled surfaces may be a reflection of each other in the plane which is perpendicular to the first axis 510.

Figure 15:
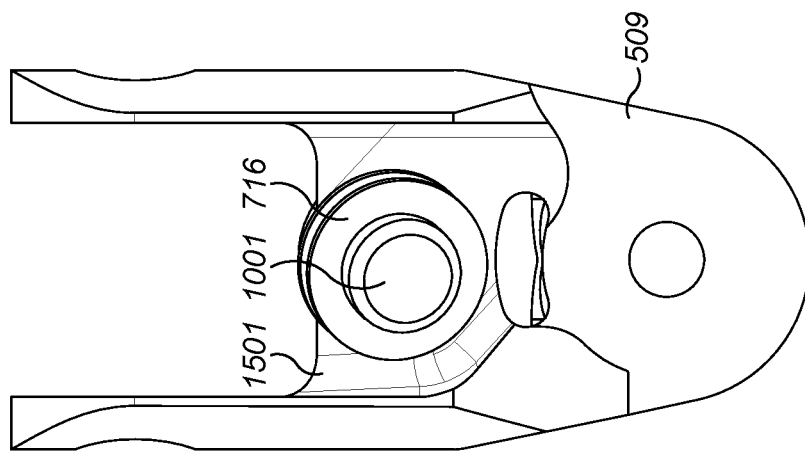
FIG. 15 illustrates a bevelled surface and groove of the supporting body of FIGS. 12 and 13.

Referring to FIG. 15, in one example, the supporting body 509 comprises grooves adjacent to each bevelled surface for seating a driving element. The supporting body comprises a groove 1501 adjacent the bevelled surface 1101 for seating the second one C2 of the third pair of driving elements. The driving element C2 is seated in the groove 1501 and partially enclosed by the first redirecting pulley 716. The supporting body comprises a groove 1502 adjacent the bevelled surface 1102 for seating the second one B2 of the second pair of driving elements. Groove 1502 is shown in FIG. 11. The driving element B2 is seated in the groove 1502 and partially enclosed by the second redirecting pulley 717.

Figure 16A:
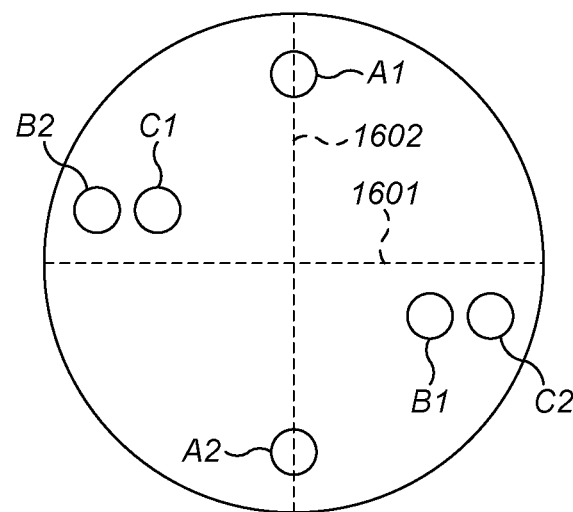
FIG. 16 illustrates arrangements of driving elements in an instrument shaft.
Figure 16B:
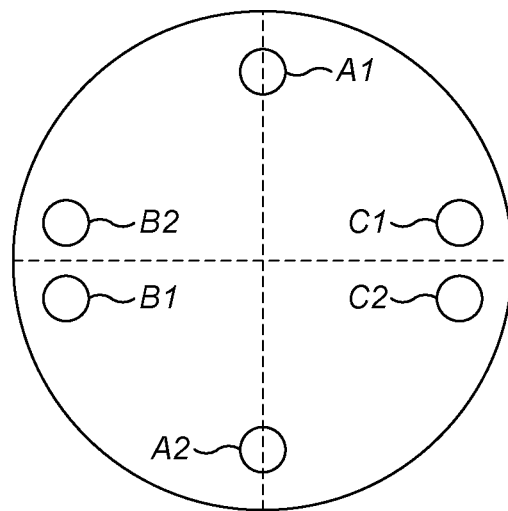

The first, second and third pairs of driving elements extend through the instrument shaft from the distal end of the shaft connected to the articulation to the proximal end of the shaft connected to a drive mechanism of the instrument interface. FIGS. 17a and 17b illustrate two views of the first, second and third pairs of driving elements extending from the described articulation to an exemplary instrument interface 1701. In an exemplary implementation, the second and third pairs of driving elements overlap in the shaft so as to emerge from the proximal end of the shaft in a different arrangement to that at which they are in at the distal end of the shaft. FIGS. 16a and 16b illustrate cross-sections of the shaft depicting the positions of the driving elements.

Configuration (a) of FIG. 16 shows a cross-section of the shaft at the distal end of the shaft. In other words, configuration (a) shows the positions of the driving elements just as they have left the second set of pulleys 602. The driving elements A1 and A2 are at opposing sides of the shaft after having left the first joint 506. The driving elements C1 and B2 are adjacent each other on an opposing side of the shaft to the driving elements B1 and C2 which are also adjacent each other. The driving elements C1 and B2 are offset from the driving elements B1 and C2 about an axis 1601 which is transverse to the axis 1602 connecting driving elements A1 and A2. This is a result of the offset axes of the two pulleys of the second set of pulleys.

Configuration (b) of FIG. 16 shows a cross-section of the shaft at the proximal end of the shaft. In other words, configuration (b) shows the positions of the driving elements as they are about to exit the shaft into the instrument interface. The first pair of driving elements A1 and A2 are on opposing sides of the shaft in a similar arrangement to their arrangement in configuration (a). The first pair of driving elements may be closer together, by virtue of them having moved slightly towards each other over the course of their extent through the shaft. In configuration (b), driving element B1 is located on an opposing side of the shaft to its location in configuration (a). In configuration (b), driving element C1 is located on an opposing side of the shaft to its location in configuration (a). To achieve this, driving element B1 and driving element C1 have not extended down the shaft parallel to the longitudinal axis of the shaft 511. Instead, driving element B1 and driving element C1 have overlapped each other during their extent in the shaft. This overlapping occurs without the driving elements B1 and C1 clashing because of their offset positions in configuration (a) owing to the pulleys of the second set of pulleys 602 having offset axes. Driving element B2 has moved a little in the shaft, but remained on the same side of the shaft as in configuration (a), so as to emerge at the proximal end of the shaft adjacent to driving element B1. Driving element C2 has moved a little in the shaft, but remained on the same side of the shaft as in configuration (a), so as to emerge at the proximal end of the shaft adjacent to driving element C1.

The instrument interface comprises a further pulley arrangement around which the first, second and third pairs of driving elements are constrained to move. The driving elements A1, A2, B1, B2, C1 and C2 emerge at the proximal end of the shaft in a configuration which enables them to engage directly with components of the instrument interface. In one implementation, the driving elements emerge at the proximal end of the shaft as shown in configuration (b) in order to engage directly with the further pulley arrangement of the instrument interface described herein. Suitably, the first, second and third driving elements extend from the pulley arrangement at the distal end of the shaft to the instrument interface without wrapping around any intervening pulleys. Suitably, there are no intervening pulleys in the shaft around which the first, second and/or third pairs of driving elements are constrained to move.

As can be seen in FIGS. 17a and 17b, the instrument interface is relatively flat. The instrument interface extends mostly in a central plane viewed head on in FIG. 17a. Suitably, the instrument shaft 504 is rigidly attached to the instrument interface 1701. The instrument shaft 504 does not rotate or otherwise move relative to the instrument interface 1701. Suitably, the second axis 512 about which the end effector elements 502, 503 rotate is perpendicular to the central plane of the instrument interface. This is the case in the straight configuration of the instrument shown in FIGS. 17a and 17b. Thus, in the straight configuration of the instrument, the jaws of the end effector are moveable in the central plane of the instrument interface.

A driving element may be a uniform component having the same shape and size along its length and constructed of the same material along its length. Alternatively, the driving element may be composed of different portions. In one example, the portion of the driving element which engages components of the instrument interface (such as pulleys and interface elements) is flexible. Similarly, the portion of the driving element which engages components of the distal end of the surgical instrument (such as the pulleys and joints in the articulation) is flexible. Between these two flexible portions are spokes 1702 illustrated in FIGS. 17a and 17b. Thus, each pair of driving elements comprises two spokes and two flexible portions. Each pair of driving elements forms a loop. The loop comprises alternating spokes and flexible portions. The two spokes are predominantly or wholly enclosed in the instrument shaft. A distal flexible portion terminates at one end in the distal end of one of the spokes, and at the other end in the distal end of the other spoke. The distal flexible portion engages components of the articulation. A proximal flexible portion terminates at one end in the proximal end of one of the spokes, and at the other end in the proximal end of the other spoke. The proximal flexible portion engages components of the instrument interface. The spokes are stiffer than the flexible portions. Suitably, the spokes are rigid. The spokes may be hollow. Typically, the spokes have a larger diameter than the flexible portions. Thus, the flexible portions may be cables, and the spokes hollow tubes. The flexible portions may terminate where they meet the spokes. Alternatively, the spokes may encapsulate the material of the flexible portions. For example, the spokes may be rigid sheaths which cover flexible cables.

The spokes are stiffer than the flexible portions. Thus, by forming a pair of driving elements from spokes as well as flexible portions, the likelihood of the driving element stretching is reduced. For this reason, the proportion of each driving element which is a spoke is preferably maximised whilst ensuring that the spoke does not come into contact with components of the articulation or the instrument interface, and also that adjacent driving elements do not collide. The spokes are stronger than the flexible portions, and hence more resilient to compression and tension forces applied in any direction than the flexible portions. Thus, by incorporating the spokes, the driving element as a whole is stiffer and less likely to stretch. Thus, the lifetime of the driving element before it needs re-tensioning or replacing is extended.

Figure 18:
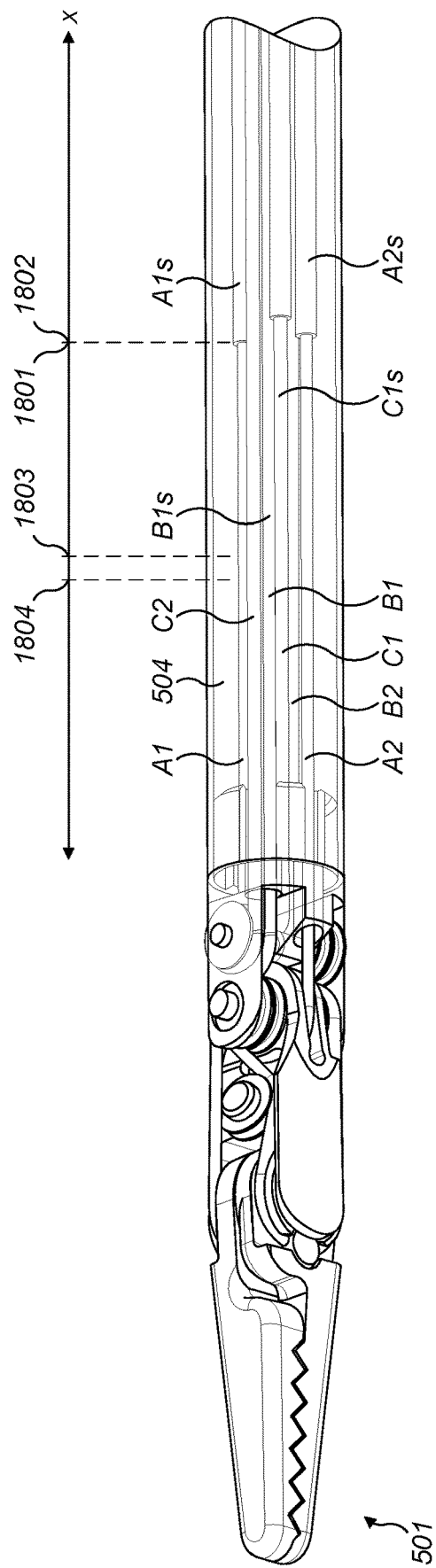
FIG. 18 illustrates spokes in an instrument shaft.

In FIG. 18 the spokes of the driving elements A1, A2, B1 and C1 are visible, labelled as A1$s$, A2$s$, B1$s$ and C1$s$ respectively. FIG. 18 depicts a straight configuration of the surgical instrument in which the end effector 501 is aligned with the shaft 504. As can be seen in FIG. 18, the distal flexible portion of driving element A1 terminates in the spoke A1$s$ at a point 1801 along the longitudinal direction x of the shaft. The longitudinal direction x is the direction of the longitudinal axis 511 of the shaft. The distal flexible portion of driving element A2 terminates in the spoke A2$s$ at a point 1802 along the longitudinal direction x of the shaft. The distal flexible portion of driving element B1 terminates in the spoke B1$s$ at a point 1803 along the longitudinal direction x of the shaft. The distal flexible portion of driving element C1 terminates in the spoke C1$s$ at a point 1804 along the longitudinal direction x of the shaft. The distal flexible portions of driving elements B2 and C2 terminate in their respective spokes further towards the proximal end of the shaft, as can be seen in FIG. 17$a$.

As can be seen in FIG. 18, the longitudinal positions 1801, 1802, 1803 and 1804 at which the distal flexible portions of the driving elements terminate in the distal ends of the spokes are not coincident when the instrument is in the straight configuration depicted. Instead, the longitudinal positions 1801, 1802, 1803 and 1804 are offset from each other. In other words, the distal ends of the spokes of the driving elements are offset along the longitudinal direction of the shaft when the instrument is in the straight configuration. Specifically, the distal ends of adjacent spokes are offset along the longitudinal direction of the shaft in the straight configuration. The distal ends of spokes which are not adjacent to each other may be coincident along the longitudinal direction of the shaft in the straight configuration. For example, in FIG. 18, the non-adjacent spokes A1$s$ and A2$s$ both terminate at the same point 1801,1802 along the longitudinal direction of the shaft. Suitably, the distal ends of the spokes of the driving elements are offset along the longitudinal direction of the shaft in every configuration of the surgical instrument. Specifically, suitably, the distal ends of adjacent spokes are offset along the longitudinal direction of the shaft in every configuration of the surgical instrument.

As previously discussed in relation to FIG. 16, the driving elements do not all extend parallel to each other in the shaft in an implementation in which driving elements pass directly from the pulley arrangement at the distal end of the shaft to the pulley arrangement in the instrument interface without moving around any intervening pulleys. The first one of the first pair of driving elements A1 extends substantially parallel to the second one of the first pair of driving elements A2 in the shaft. Driving elements A1 and A2 may move slightly closer to each other over the course of the length of the shaft in the direction from the articulation to the instrument interface. The first one of the second pair of driving elements B1 extends at an angle to the second one of the second pair of driving elements B2 in the shaft. Driving element B1 also extends at an angle to driving elements A1, A2, C1 and C2 down the shaft. Driving element B2 extends at an angle to driving elements A1, A2, C1 and C2 down the shaft.

The first one of the third pair of driving elements C1 extends at an angle to the second one of the third pair of driving elements C2 in the shaft. Driving element C1 also extends at an angle to driving elements A1, A2, B1 and B2 down the shaft. Driving element C2 extends at an angle to driving elements A1, A2, B1 and B2 down the shaft.

The longitudinal positions of the distal ends of the spokes are selected such that the spokes do not collide when the instrument is being articulated. Since the spokes have a larger diameter than the flexible portions, although the flexible portions can extend down the length of the shaft without colliding the spokes may not be able to. Suitably, the longitudinal positions of the distal ends of the spokes in the straight configuration of the instrument are such that for any configuration of the end effector, no portion of any driving element contacts a portion of another driving element. Suitably, the positions of the proximal and distal ends of the spokes in the straight configuration are selected so as to maximise the spoke length whilst satisfying the condition that the driving elements will not contact. The spokes are stiffer than the flexible portions. Thus, this maximises the stiffness of the driving elements whilst enabling them to wrap around components in the articulation and instrument interface. This maximises the strength of the driving elements whilst enabling them to wrap around components in the articulation and instrument interface.

Figure 19A:
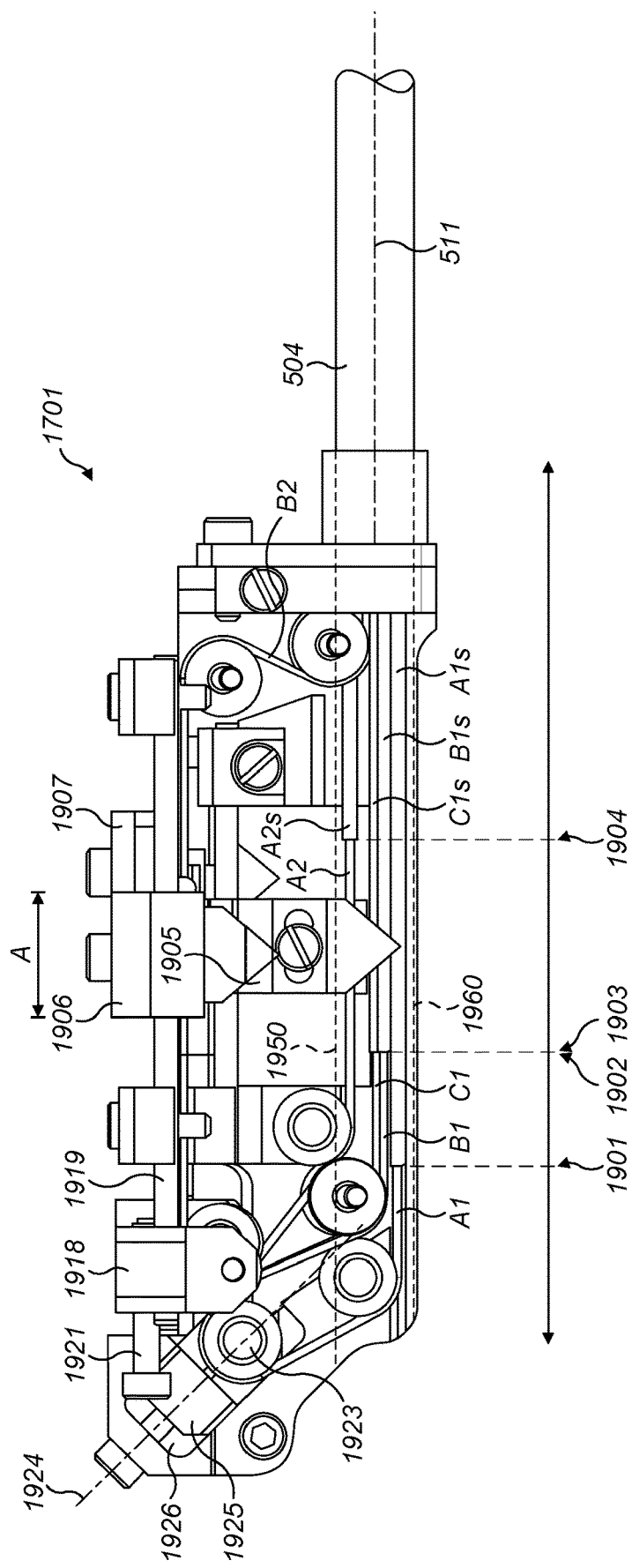
FIGS. 19a, 19b and 19c illustrate three views of an instrument interface.

In FIG. 19$a$ the spokes of the driving elements A1, A2, B1 and C1 are visible, labelled as A1$s$, A2$s$, B1$s$ and C1$s$ respectively. FIG. 19$a$ depicts a non-straight configuration of the surgical instrument in which the end effector 501 is not aligned with the shaft 504. As can be seen in FIG. 19$a$, the proximal flexible portion of driving element A1 terminates in the spoke A1$s$ at a point 1901 along the longitudinal direction x of the shaft. The longitudinal direction x is the direction of the longitudinal axis 511 of the shaft. The proximal flexible portion of driving element A2 terminates in the spoke A2$s$ at a point 1904 along the longitudinal direction x of the shaft. The proximal flexible portion of driving element B1 terminates in the spoke B1$s$ at a point 1902 along the longitudinal direction x of the shaft. The proximal flexible portion of driving element C1 terminates in the spoke C1s at a point 1903 along the longitudinal direction x of the shaft. The proximal flexible portions of driving elements B2 and C2 terminate in their respective spokes further towards the distal end of the shaft, as can be seen in FIG. 17*a*. The spokes may terminate in the proximal flexible portions inside the shaft, as is the case in the example shown for driving elements B2 and C2. The spokes may terminate in the proximal flexible portions inside the instrument interface, as is the case in the example shown for driving elements A1, A2, B1 and C1. Some spokes may terminate in the proximal flexible portions inside the shaft and some spokes may terminate in the proximal flexible portions inside the instrument interface. In the design of the instrument interface depicted in FIG. 19*a*, the driving elements B2 and C2 engage pulleys as they enter the instrument interface from the shaft, thus the spokes of driving elements B2 and C2 terminated in their proximal flexible portions in the shaft (not shown) to enable the proximal flexible portions to engage the pulleys. Driving elements A1, A2, B1 and C1 all extend some distance into the instrument interface before engaging with components of the instrument interface, thus the spokes of driving elements A1, A2, B1 and C1 are able to extend into the instrument interface.

As can be seen in FIG. 19*a*, the longitudinal positions 1901, 1902, 1903 and 1904 at which the proximal flexible portions of the driving elements terminate in the proximal ends of the spokes are not coincident. Instead, the longitudinal positions 1901, 1902, 1903 and 1904 are offset from each other. In other words, the proximal ends of the spokes of the driving elements are offset along the longitudinal direction of the shaft when the instrument is in the configuration shown. Suitably, the proximal ends of the spokes of the driving elements are offset along the longitudinal direction of the shaft for the straight configuration of the instrument. Specifically, the proximal ends of adjacent spokes are offset along the longitudinal direction of the shaft in the straight configuration. The proximal ends of spokes which are not adjacent to each other may be coincident along the longitudinal direction of the shaft in the straight configuration. For example, in FIG. 19*a*, the non-adjacent spokes B1s and C1s both terminate at the same point 1902,1903 along the longitudinal direction of the shaft. Suitably, the proximal ends of the spokes of the driving elements are offset along the longitudinal direction of the shaft in every configuration of the surgical instrument. Specifically, suitably, the distal ends of adjacent spokes are offset along the longitudinal direction of the shaft in every configuration of the surgical instrument.

The longitudinal positions of the proximal ends of the spokes are selected such that the spokes do not collide when the instrument is being articulated. Suitably, the longitudinal positions of the proximal ends of the spokes in the straight configuration of the instrument are such that for any configuration of the end effector, no portion of any driving element contacts a portion of another driving element.

Each pair of driving elements engages a single instrument interface element in the instrument interface. Each driving element engages an instrument interface element in the instrument interface. In the example illustrated in FIGS. 19*a*, 19*b* and 19*c*, each driving element engages its own instrument interface elements. A single instrument interface element drives a pair of driving elements. Each driving element is driven independently by a single instrument interface. In alternative arrangements, there may be a compound driving motion in which more than one instrument interface element drives a single driving element, a single instrument interface element drives more than one pair of driving elements, or a plurality of instrument interface elements collectively drive a plurality of driving elements.

Figure 19B:
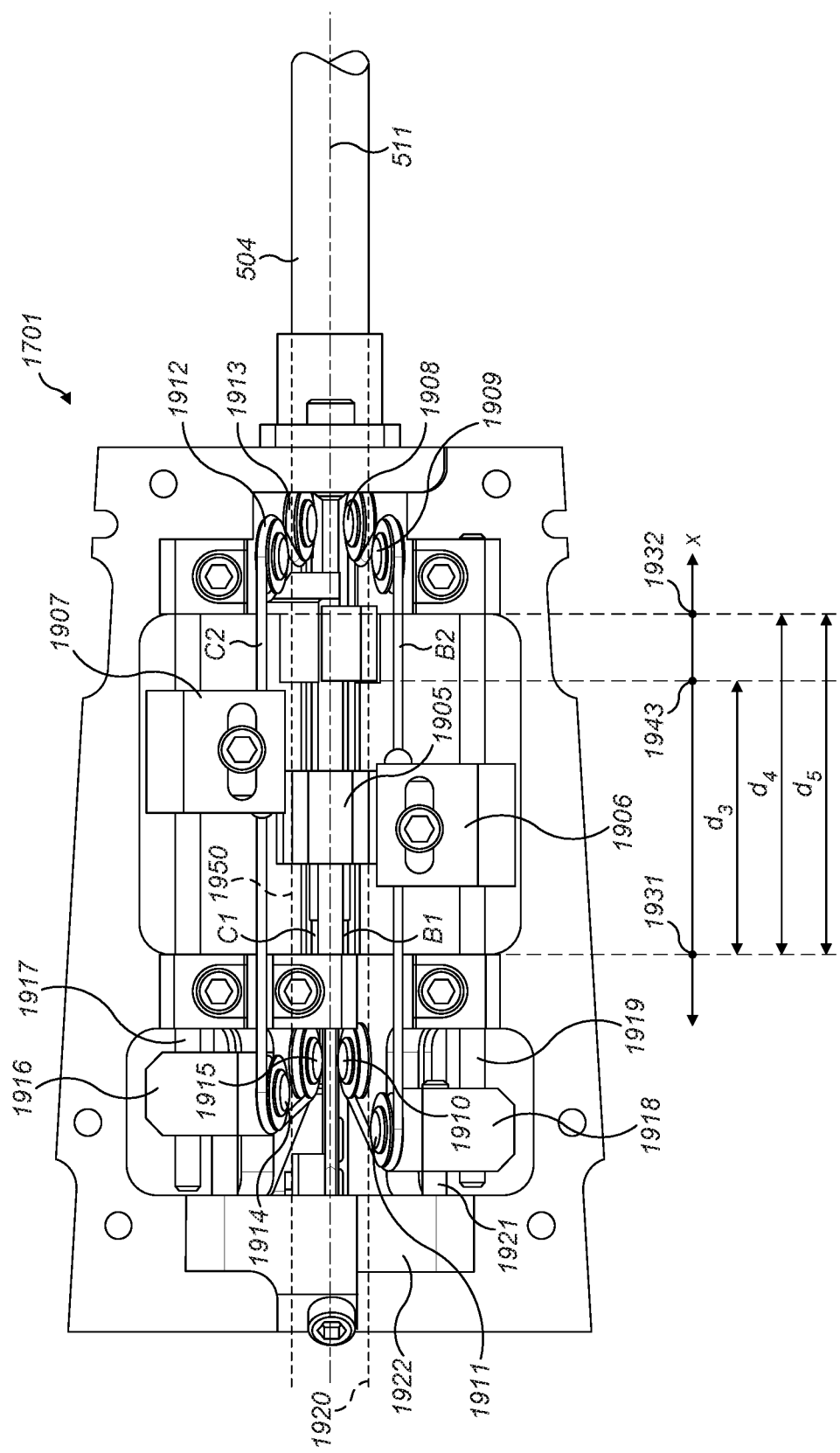

FIG. 19*b* illustrates a first instrument interface element 1905 which engages the first pair of driving elements A1,A2. A second instrument interface element 1906 engages the second pair of driving elements B1,B2. A third instrument interface element 1907 engages the third pair of driving elements C1,C2. Suitably, each driving element is secured to its associated instrument interface element. In other words, each driving element is fast with its associated instrument interface element.

The instrument interface 1701 has a significantly larger profile than the instrument shaft 504. Typically, the instrument shaft has a circular cross-section having a diameter of less than or the same as 5 mm, whereas a corresponding cross-section through the instrument interface may be larger than this. The instrument interface comprises an internal portion and an external portion. The internal portion is bounded by the dotted line 1950 (shown in FIGS. 19*a* and 19*b*). The external portion is the remainder of the instrument interface which is not in the internal portion. The internal portion is within the projected profile of the shaft. In other words, the internal portion is the part of the instrument interface that would have been encompassed had the profile of the shaft continued within the instrument interface. The external portion is outside of the projected profile of the shaft. In the example illustrated, the shaft has a constant circular cross-section, and hence the internal portion is a cylinder having the same circular cross-section as the shaft, and having the same longitudinal axis 511 as the shaft. In other words, the internal portion is an extrapolation of the constant cross-section of the shaft in the instrument interface. The internal portion 1950 is shown from the side in FIG. 19*a* and from the top in FIG. 19*b*.

The instrument interface elements 1905, 1906 and 1907 are dispersed across the width of the instrument interface as shown in FIG. 19*b*. In the arrangement depicted in FIG. 19*b*, one instrument interface element 1905 is within the internal portion 1950 of the instrument interface. Specifically, the part of the instrument interface element 1905 which engages the driving element is within the internal portion 1950 of the instrument interface. The instrument interface element 1905 as a whole may be substantially within the internal portion 1950 of the instrument interface, as shown in FIG. 19*b*. The instrument interface element 1905 as a whole may be wholly within the internal portion 1950 of the instrument interface. Suitably, the instrument interface element 1905 is aligned with the longitudinal axis 511 of the shaft 504. In an exemplary arrangement, only one instrument interface element is located within the internal portion of the instrument interface. The remainder of the instrument interface elements 1906, 1907 are within the external portion of the instrument interface. These other instrument interface elements 1906, 1907 are located on either side of the aligned instrument interface element 1905. Specifically, the other instrument interface elements 1906, 1907 are located on either side of the aligned instrument interface element 1905 in a direction perpendicular to the longitudinal axis of the shaft 511. The instrument interface elements 1906 and 1907 are not aligned with the longitudinal axis 511 of the shaft 504. The instrument interface elements 1906 and 1907 are constrained to move parallel to the longitudinal axis 511 of the shaft 504, since they are constrained to move along rails 1929 and 1930 respectively.

Instrument interface element 1905 engages a first pair of driving elements A1, A2. As can be seen in FIG. 19*a*, between the proximal end of the shaft and the instrument interface element 1905, the pair of driving elements A1, A2 lie wholly within the internal portion 1950. Between the proximal end of the shaft and the instrument interface element 1905, the pair of driving elements A1, A2 lie wholly parallel to the longitudinal axis of the shaft 511. Suitably, there are no intervening pulleys or other structures in the instrument interface around which the pair of driving elements A1, A2 is constrained to move between the proximal end of the shaft and the instrument interface element 1905. Suitably, only instrument interface element 1905 engages its pair of driving elements A1, A2 in the internal portion 1950 of the instrument interface.

Instrument interface element 1906 engages a second pair of driving elements B1, B2. The instrument interface element 1906 engages the second pair of driving elements B1, B2 in the external portion of the instrument interface.

Instrument interface element 1907 engages a third pair of driving elements C1, C2. The instrument interface element 1907 engages the third pair of driving elements C1, C2 in the external portion of the instrument interface.

A pulley arrangement is used to shift the driving elements over to engage with the instrument interface elements which are in the external portion. Each pair of driving elements engages a first pair of pulleys to shift it over from the proximal end of the shaft 504 to its respective instrument interface element, and a second pair of pulleys to shift it back from alignment with the instrument interface element to alignment with the shaft 504.

In the arrangement shown, the second pair of driving elements B1,B2 emerges from the proximal end of the shaft in a direction aligned with the shaft. The driving elements B1,B2 do not run exactly parallel to the longitudinal axis 511 of the shaft 504 as a result of the direction changes described with respect to FIG. 16. The second pair of driving elements B1, B2 is then constrained to move around pulley pair 1908 and 1909 to shift it from where it emerges from the shaft 504 to engagement with the second instrument interface element 1906. The second pair of driving elements B1, B2 emerges from the pulley pair 1908 and 1909 in a direction parallel to and offset from the direction that the second pair of driving elements B1, B2 emerges from the proximal end of the shaft. The second pair of driving elements B1,B2 is constrained to move around pulley pair 1910 and 1911 to shift it from alignment with the second instrument interface element 1906 to alignment with the shaft 504.

In the arrangement shown, the third pair of driving elements C1, C2 emerges from the proximal end of the shaft in a direction aligned with the shaft. The driving elements C1,C2 do not run exactly parallel to the longitudinal axis 511 of the shaft 504 as a result of the direction changes described with respect to FIG. 16. The third pair of driving elements C1,C2 is then constrained to move around pulley pair 1912 and 1913 to shift it from where it emerges from the shaft 504 to engagement with the third instrument interface element 1907. The third pair of driving elements C1, C2 emerges from the pulley pair 1912 and 1913 in a direction parallel to and offset from the direction that the third pair of driving elements C1, C2 emerges from the proximal end of the shaft. The third pair of driving elements C1,C2 is constrained to move around pulley pair 1914 and 1915 to shift it from alignment with the third instrument interface element 1907 to alignment with the shaft 504.

Figure 19C:
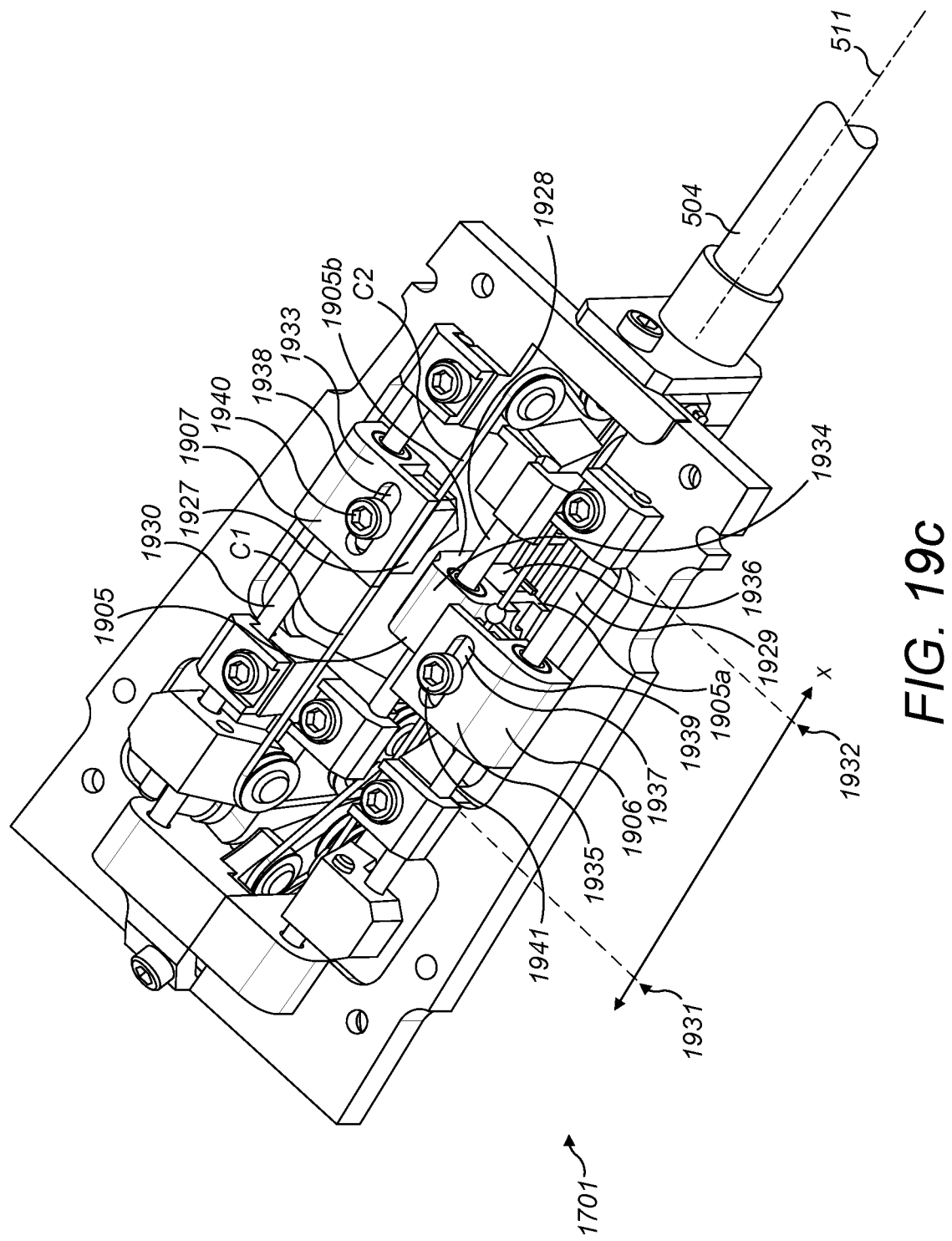

In the arrangement shown in FIGS. 19a, 19b and 19c, pair of driving elements A1, A2 engage with the first instrument interface element 1905 which is within the internal portion. Pair of driving elements A1, A2 drive rotation of the articulation, and hence the end effector, about the first axis 510 (see figure 5a). There is a smaller range of motion about first joint 506 than there is about second joint 507 and third joint 513. As described below, the first instrument interface element 1905 is linearly displaceable through a maximum distance $d_3$ minus the length of the first instrument interface element 1905, which is smaller than the maximum displacement of the second instrument interface element 1906 $d_4$ minus the length of the second instrument interface element 1906, and smaller than the maximum displacement of the third instrument interface element 1907 $d_5$ minus the length of the third instrument interface element 1907. Since motion about the first joint 506 is controlled via a shorter range of travel of the instrument interface element than the second and third joints, greater sensitivity of that motion is preferred. Cables may slip and/or stretch over pulleys. Thus, the simplest cabling scheme is preferably utilised for transferring motion between the first instrument interface element and the first joint 506.

By locating the first instrument interface element 1905 within the internal portion on the longitudinal axis of the shaft 511, the first pair of driving elements is not constrained to pass around any intervening pulleys between the first joint 506 and the first instrument interface element 1905.

Each instrument interface element is displaceable within the instrument interface. Since each instrument interface element is secured to a corresponding pair of driving elements, a displacement of the instrument interface element is transferred to a displacement of the pair of driving elements. Suitably, each instrument interface element is displaceable along the same line as the line of the pair of driving elements that it is secured to. Each instrument interface element engages with a corresponding drive assembly interface element of the robot arm. Thus, displacement of the instrument interface element is driven by the robot arm. In this way, the robot arm drives the pairs of driving elements.

Each pair of driving elements engages with an instrument interface element in the instrument interface. The pair of driving elements also engages with a tensioning mechanism and an alignment mechanism. When manufacturing the instrument, the tensioning mechanism is used to achieve a desired tension in the pair of driving elements. The alignment mechanism is used to set the instrument interface elements to a predetermined alignment position in the longitudinal direction of the shaft when the end effector has a predetermined configuration. Each instrument interface element has a displacement range over which it is displaceable. The predetermined alignment position may be the midpoint of the displacement range for each instrument interface element. The predetermined configuration of the end effector may be the straight configuration, in which the end effector elements are closed together (for example the jaws are closed), and the longitudinal axis of the articulation and the longitudinal axis of the end effector are aligned with the longitudinal axis of the shaft 511. By setting the instrument interface elements to a predetermined alignment position when the end effector has a predetermined configuration, when changing instruments during an operation, the time taken to set up the new instrument ready for use may be reduced. In practice, when an instrument is removed from the robot arm, the robot arm assembly may be configured to go to an arrangement in which it is ready to receive the instrument interface elements in the predetermined alignment position. For example, the robot arm assembly interface elements may go to a default position in which they are arranged to receive each of the instrument interface elements at the midpoint of their displacement range. Then, the instrument is manually put in the predetermined configuration and then slotted into the robot arm. For example, the technician moves the articulation and end effector into the straight configuration and then slots the instrument into the robot arm. Because it is known that the instrument interface elements have the predetermined alignment position when the instrument is in the predetermined configuration, the instrument interface elements engage directly with the robot arm assembly interface elements. The control system does not need to perform an additional calibration or software setup procedure in order to map the position and orientation of the end effector, because it is known that the end effector is in the predetermined configuration.

The following describes tensioning and alignment mechanisms which are independent of each other. By isolating the tensioning mechanism from the alignment mechanism the process by which the desired tension and desired alignment are achieved is simplified. Thus, the time taken to achieve the desired tension and desired alignment during manufacture is reduced.

FIGS. 19a, 19b and 19c illustrate a tensioning mechanism utilising pulleys. Each pair of driving elements is independently tensioned. Each pair of driving elements is constrained to move around a pulley which is displaceable. FIGS. 19a, 19b and 19c depict two different exemplary pulley arrangements for tensioning the pairs of driving elements. In both examples, the pulley is linearly displaceable.

Referring firstly to the tensioning mechanism shown for the pairs of driving elements B1,B2 and C1,C2. Taking pair of driving elements B1,B2 first, pulley 1911 is used to tension B1,B2.

Pulley 1911 is linearly displaceable along a displacement axis 1920 which is parallel to the longitudinal axis 511 of the shaft. The displacement axis 1920 is offset from the longitudinal axis 511 of the shaft. Displacement axis 1920 is shown in FIG. 19b. The tensioning pulley 1911 is mounted to a block 1918 which is slideable along a rail 1919. Sliding the block 1918 along the rail 1919 causes the pulley 1911 to displace along the displacement axis 1920. When the block 1918 is moved away from the shaft, the tension of the second pair of driving elements B1,B2 increases. When the block 1918 is moved towards the shaft, the tension of the second pair of driving elements B1,B2 decreases. Any suitable mechanism may be used to move the block. For example, a screw adjustment mechanism may be used. FIGS. 19a, 19b and 19c show a screw adjustment mechanism in which screw 1921 is threaded into block 1918. This is most clearly seen on FIG. 19a. The screw 1921 is constrained by portion 1922 of the instrument interface such that it is able to rotate but not able to be displaced linearly. Thus, when the screw is rotated, the screw thread engages with the thread inside the block 1918 causing the block and hence the pulley 1911 to displace linearly. When the screw 1921 is tightened, the pulley 1911 moves in one linear direction. When the screw 1921 is loosened, the pulley 1911 moves in the opposing linear direction. The tensioning mechanism for driving elements C1,C2 depicted in FIGS. 19a, 19b and 19c works in a corresponding manner to that described with relation to driving elements B1,B2.

Referring now to the tensioning mechanism shown for the first pair of driving elements A1,A2 in FIG. 19a. Pulley 1923 is used to tension A1,A2. Pulley 1923 is linearly displaceable along a displacement axis 1924. Displacement axis 1924 is at an angle to the longitudinal axis 511 of the shaft. Suitably, the displacement axis 1924 may be at a 45° angle to the longitudinal axis 511 of the shaft. The tensioning pulley 1923 is mounted to a block 1925 which is captive in a socket 1926 of the instrument interface. The block 1925 and tensioning pulley 1923 are able to slide through the socket 1926. Sliding the block 1925 through the socket 1926 causes the pulley to displace along the displacement axis 1924. When the block 1925 is slid further into the socket, the tension of the first pair of driving elements A1,A2 increases. When the block 1925 is slid out of the socket, the tension of the first pair of driving elements A1,A2 decreases. Any suitable mechanism may be used to move the block 1925. For example, a screw adjustment mechanism as described above with respect to block 1918 may be used. Since the first pair of driving elements A1,A2 wrap almost fully around tensioning pulley 1923 such that they run almost parallel to each other, a greater tension is applied per unit displacement of the tensioning pulley compared to the tensioning mechanism described with respect to the second and third pairs of driving elements.

Although FIGS. 19a, 19b and 19c show the first pair of driving elements using the angled tensioning mechanism, and the second and third pairs of driving elements using the linear tensioning mechanism, any pair of driving elements may be tensioned using any suitable mechanism as long as that mechanism packages into the instrument interface.

Figure 20A:
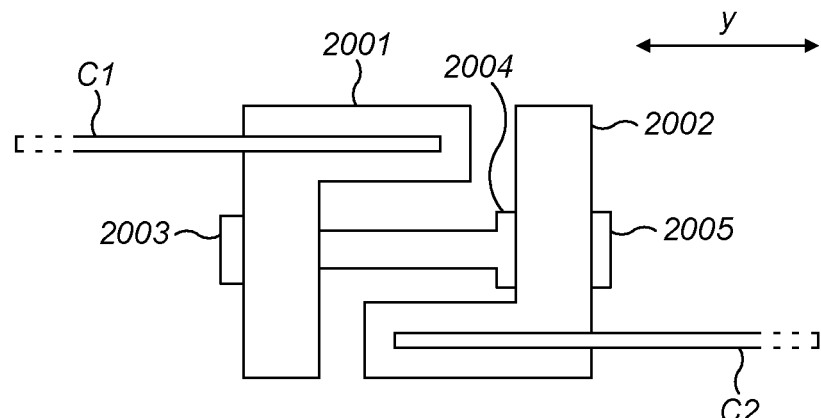
FIGS. 20a and 20b illustrate tensioning mechanisms.

FIG. 20a illustrates an alternative tensioning mechanism. Each pair of driving elements terminates in a lug 1927 of an instrument interface element (see FIG. 19c). FIG. 20a illustrates an alternative arrangement of lug 1927 to that shown in FIG. 19c. In the arrangement of FIG. 20a, the lug is utilised in the tensioning mechanism. The lug of FIG. 20a has a pair of lug elements 2001 and 2002. One driving element of a pair of driving elements terminates in one lug element, and the other driving element of the pair of driving elements terminates in the other lug element. A first one of the third pair of driving elements C1 has been depicted as terminating in lug element 2001, and the second one of the third pair of driving elements C2 has been depicted as terminating in lug element 2002. The pair of lug elements are coupled so as to be linearly displaceable with respect to each other. Suitably, the pair of lug elements are linearly displaceable along the direction y of the pair of driving elements to which they are attached. Suitably, the pair of lug elements are displaceable along a displacement axis that is parallel to and offset from the longitudinal axis 511 of the shaft. The lug elements 2001 and 2002 may be coupled by any suitable mechanism which is able to move the lug elements relative to each other along the displacement axis. For example, the lug elements may be coupled together by a screw 2003. The screw 2003 is captive in a first lug element 2002 and constrained by the first lug element 2002 so as to prevent the screw 2003 from displacing linearly with respect to the first lug element 2002. For example, as shown in FIG. 20a, the screw may pass through a hole in the first lug element in which it is able to rotate, and be constrained from linearly displacing through the first lug element by two portions 2004 and 2005 which have a larger diameter than the hole through the first lug element. The screw 2003 is threaded through the second lug element 2001. Thus, the lug elements 2001 and 2002 displace linearly towards each other when the screw is tightened, and displace linearly away from each other when the screw is loosened.

Figure 20B:
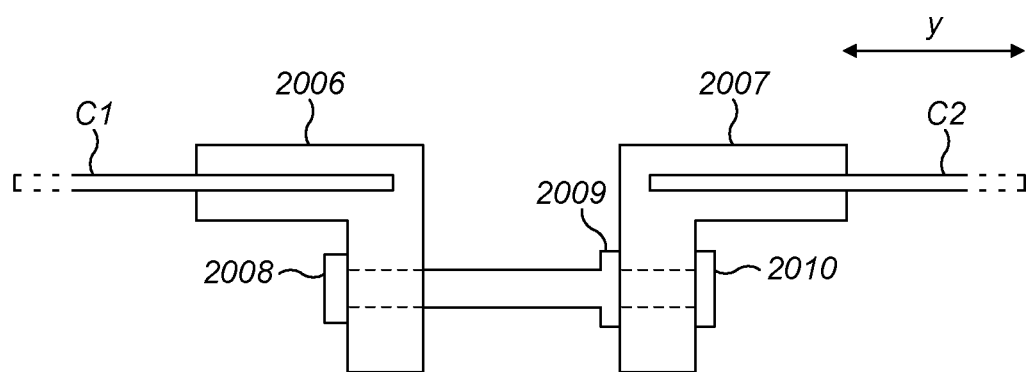

FIG. 20b illustrates a further alternative tensioning mechanism. FIG. 20b illustrates a further alternative arrangement of lug 1927 to that shown in FIG. 19c. In the arrangement of FIG. 20b, the lug is utilised in the tensioning mechanism. The lug of FIG. 20b has a pair of lug elements 2006 and 2007. One driving element of a pair of driving elements terminates in one lug element, and the other driving element of the pair of driving elements terminates in the other lug element. A first one of the third pair of driving elements C1 has been depicted as terminating in lug element 2006, and the second one of the third pair of driving elements C2 has been depicted as terminating in lug element 2007. The pair of lug elements are coupled so as to be linearly displaceable with respect to each other. Suitably, the pair of lug elements are linearly displaceable along the direction y of the pair of driving elements to which they are attached. Suitably, the pair of lug elements are displaceable along a displacement axis that is parallel to and offset from the longitudinal axis 511 of the shaft. The lug elements 2006 and 2007 may be coupled by any suitable mechanism which is able to move the lug elements relative to each other along the displacement axis. For example, the lug elements may be coupled together by a screw 2008. The screw 2008 is captive in a first lug element 2007 and constrained by the first lug element 2007 so as to prevent the screw 2008 from displacing linearly with respect to the first lug element 2007. For example, as shown in FIG. 20b, the screw may pass through a hole in the first lug element in which it is able to rotate, and be constrained from linearly displacing through the first lug element by two portions 2009 and 2010 which have a larger diameter than the hole through the first lug element. The screw 2008 is threaded through the second lug element 2006. Thus, the lug elements 2006 and 2007 displace linearly towards each other when the screw is tightened, and displace linearly away from each other when the screw is loosened.

Referring to FIG. 19c, each instrument interface element 1905, 1906 and 1907 is linearly displaceable parallel to the longitudinal axis of the shaft 511. The instrument interface element may be slideable along a linear rail. For example, first instrument interface element 1905 is slideable along rail 1928, second instrument interface element 1906 is slideable along rail 1929, and third instrument interface element 1907 is slideable along rail 1930. Each instrument interface element can be displaced over a displacement range between a minimum displacement position and a maximum displacement position. For example, the minimum and maximum displacement positions may be determined by the ends of the rail along which the instrument interface element slides in the longitudinal direction x of the shaft. The minimum and maximum displacement positions are labelled 1931 and 1932 on FIGS. 19b and 19c for the second and third instrument interface elements 1906 and 1907. The minimum and maximum displacement positions are labelled 1931 and 1943 on FIG. 19b for the first instrument interface element 1905. The first instrument interface element is linearly displaceable through a maximum distance $d_3$ minus the length of the first instrument interface element in the direction x. The second instrument interface element is linearly displaceable through a maximum distance $d_4$ minus the length of the second instrument interface element in the direction x. The third instrument interface element is linearly displaceable through a maximum distance $d_5$ minus the length of the third instrument interface element in the direction x. Suitably $d_3 < d_4$ and $d_3 < d_5$. Suitably, $d_4 = d_5$.

Suitably, in the straight configuration of the instrument in which the end effector is aligned with the shaft, the first, second and third instrument interface elements 1905, 1906 and 1907 are all located in the same plane perpendicular to the longitudinal axis of the shaft. Alternatively, in the straight configuration of the instrument, the first instrument interface element 1905 may be centred in a different plane to the plane in which the second and third instrument interface elements 1906, 1907 are centred. This is because the midpoint of the travel of the first instrument interface element 1905 over $d_3$ is offset from the midpoint of the travel of the second and third instrument interface elements 1906, 1907 over $d_4$, $d_5$.

Suitably, each instrument interface element comprises a body 1933, 1934, 1935 and a lug 1927, 1936, 1937. The body 1933, 1934, 1935 is linearly displaceable between the minimum displacement position and the maximum displacement position of the instrument interface element. The pair of driving elements which engages the instrument interface element is secured to the lug of the instrument interface element. The lug is linearly displaceable within the body parallel to the direction along which the body is displaceable. Suitably, the lug is linearly displaceable along the longitudinal direction x of the shaft parallel to the longitudinal axis 511 of the shaft. The alignment mechanism adjusts the displacement position of the body without displacing the lug. For example, the alignment mechanism may comprise a screw adjustment mechanism coupled to the body and lug which enables the body to move without moving the lug. FIG. 19c depicts such a screw adjustment mechanism. The body 1933, 1935 comprises a slot 1938, 1939 aligned with the direction along which the body is displaceable. A screw 1940, 1941 is threaded into the lug through the slot 1938, 1939. The screw 1940, 1941 is constrained to slide along the slot. For example, the screw head may be too large to pass through the slot and the screw body a loose fit through the slot. Thus, the when the screw is loose, the body is displaceable relative to the lug along the width of the slot. When the screw is tight, the body is held fast with the lug. Thus, the relative position of the body and the lug can be adjusted by the width of the slot.

The following describes steps to be carried out during manufacture following assembly of the instrument in order to set the tension of the driving elements and the alignment of the instrument interface elements.

Initially, the instrument interface is loosened from the driving elements. The instrument interface elements are set to the alignment position. For example, if the alignment position is with each instrument interface element at the mid-point of its travel over its displacement range, then the instrument interface elements are aligned to these positions. This initial step may be a rough alignment of the instrument interface elements to their alignment positions. Alternatively, this initial step may not be carried out. Next, the end effector is placed in the predetermined configuration. Next, the pairs of driving elements are tensioned. This may be done using any of the tensioning mechanisms described herein, for example by sliding a tensioning pulley along a rail or through a socket, or by displacing a pair of lug elements. Once tensioned, the displacement position of the instrument interface element is then set to the predetermined alignment position using the alignment mechanism. For example, in the implementation shown in FIGS. 19a, 19b and 19c, the screw 1940, 1941 is loosened, and the body 1933, 1935 of the instrument interface element displaced along the rail 1930, 1929 relative to the lug 1938, 1937 until the body of the instrument interface element is in the predetermined alignment position. The end effector may be held in the predetermined configuration whilst the pairs of driving elements are tensioned. Alternatively, or additionally, the end effector may be returned to the predetermined configuration after the pairs of driving elements have been tensioned. The screw is then tightened.

Figure 21A:
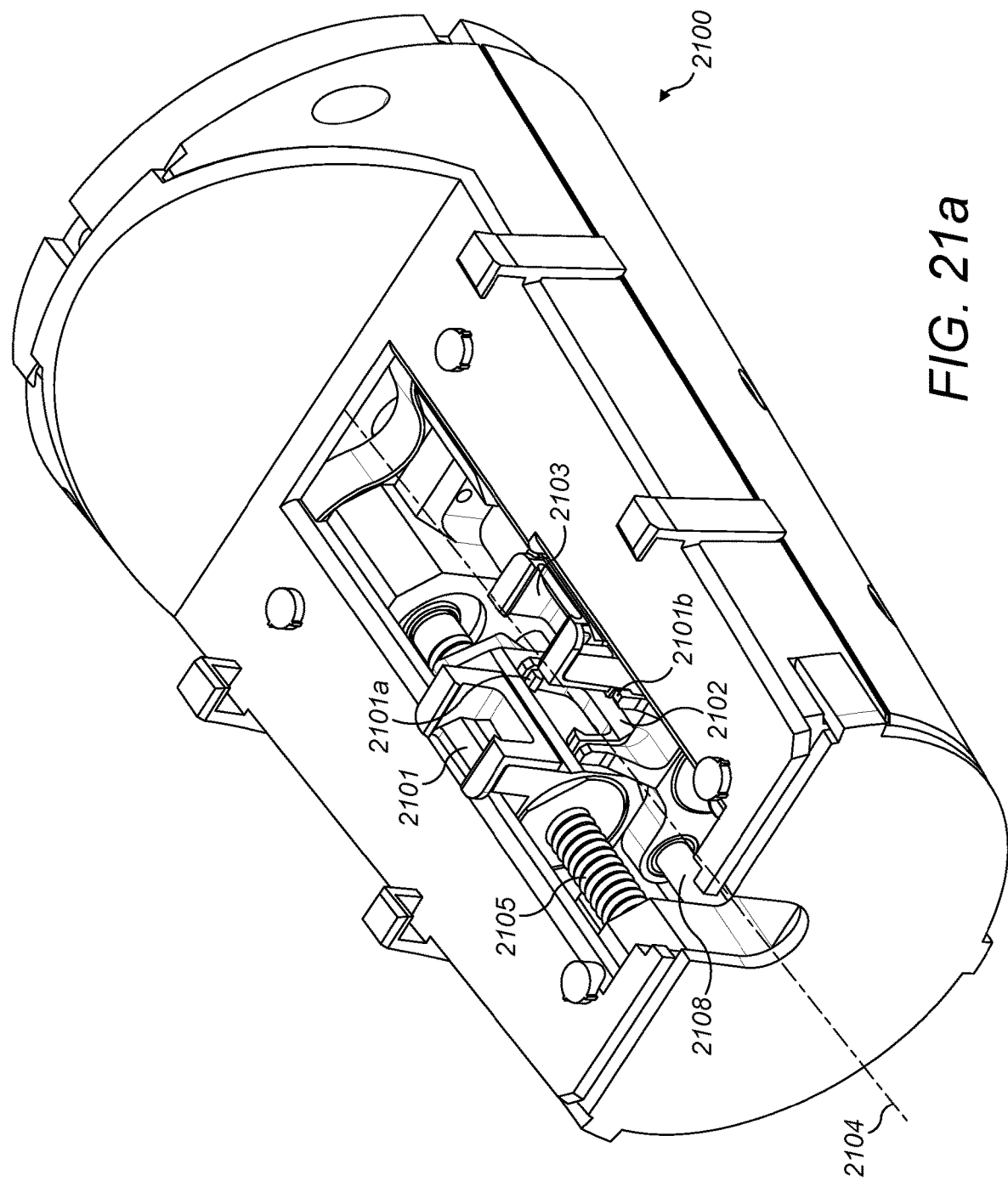
FIGS. 21a, 21b and 21c illustrate three views of a drive assembly interface of a robot arm.
Figure 21B:
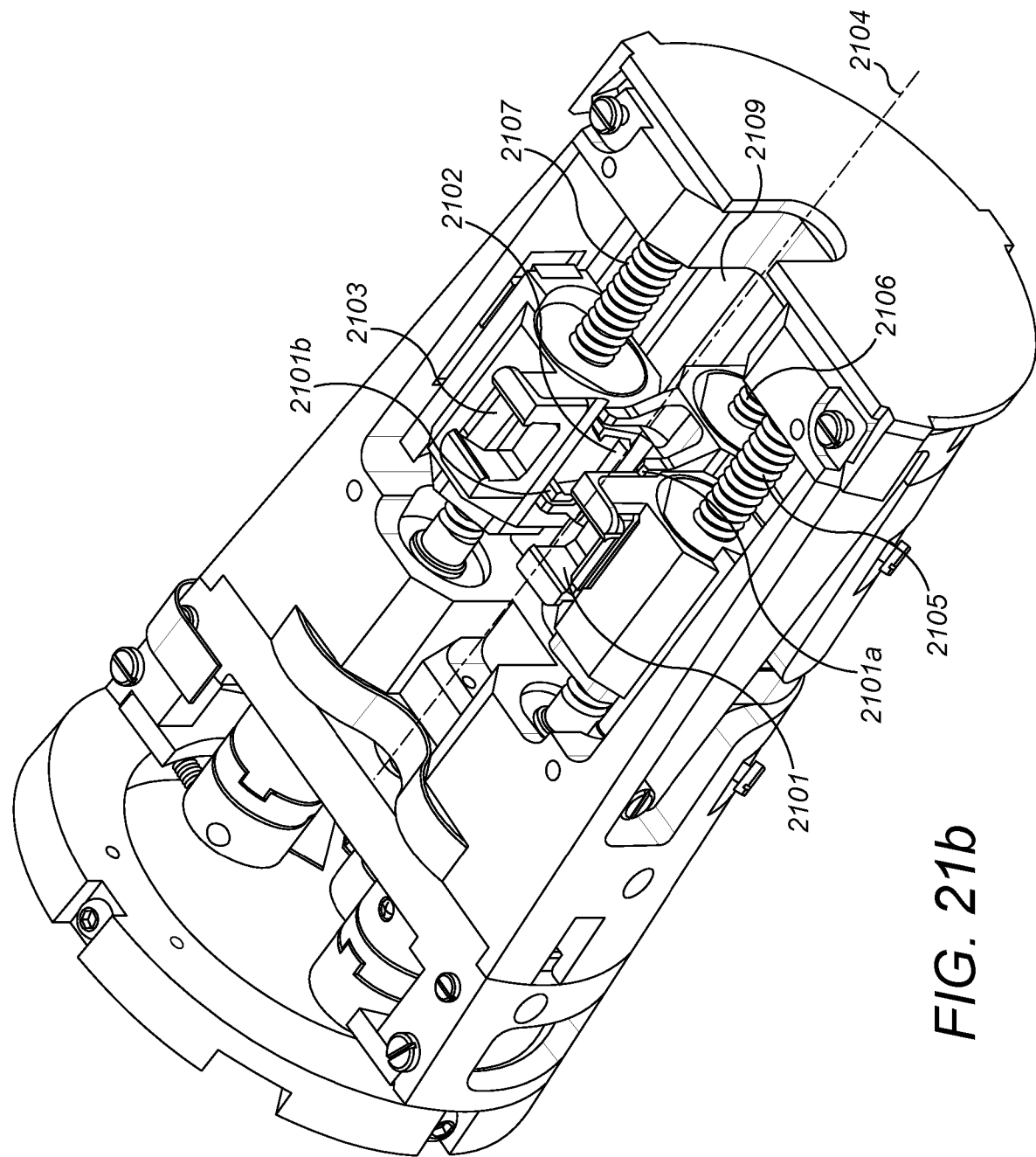
Figure 21C:
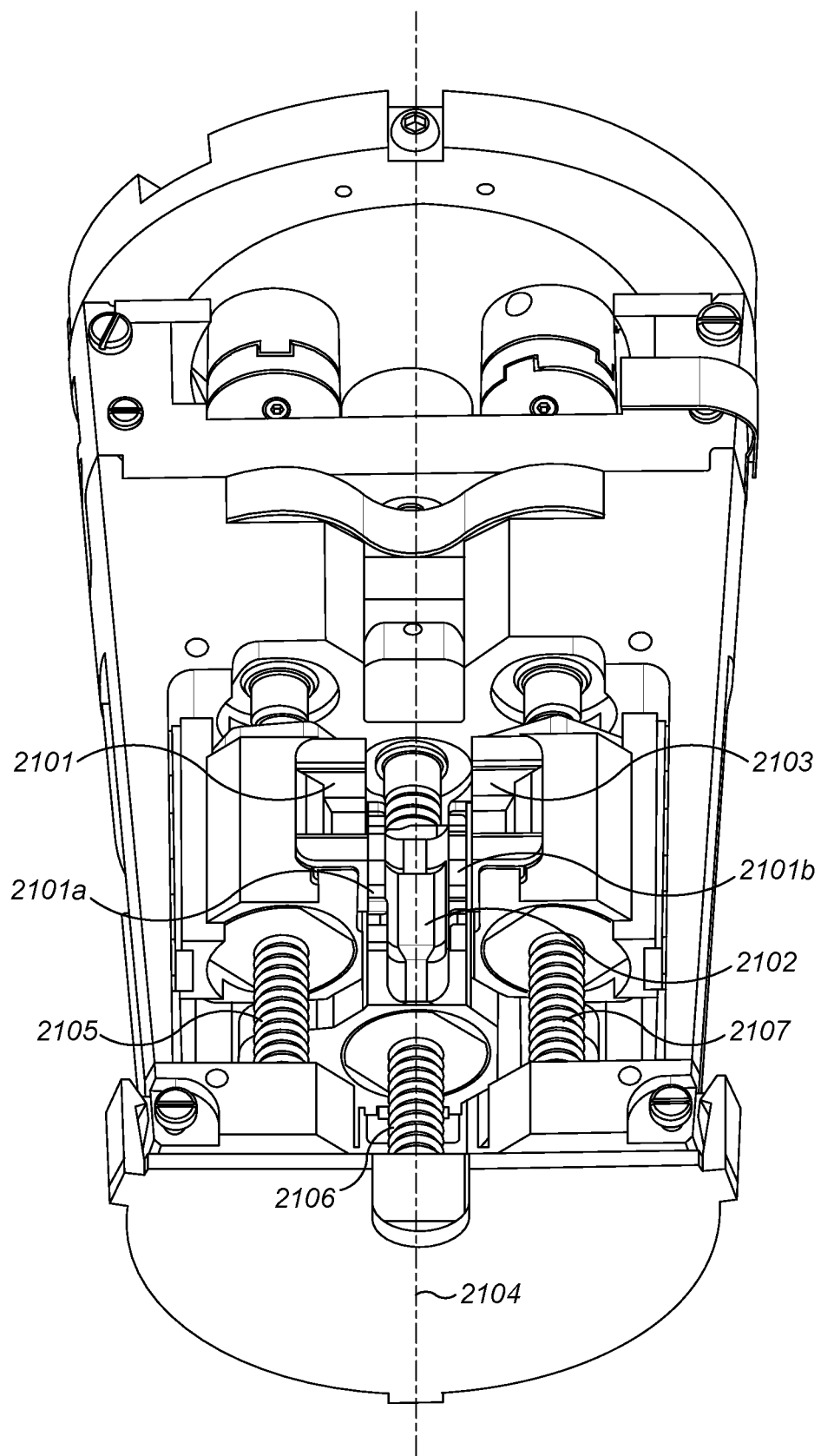

FIGS. 21a, 21b and 21c illustrates a drive assembly interface 2100. The drive assembly interface is at the terminal end of the terminal link of the robot arm. That terminal link is connected to the link next to it by a roll joint. The roll joint permits the terminal link to rotate about a longitudinal axis 2104 of the terminal link. Drive assembly interface 2100 comprises drive assembly interface elements 2101, 2102 and 2103. The drive assembly interface elements are configured to receive instrument interface elements 1905, 1906 and 1907. First drive assembly interface element 2102 is configured to receive first instrument interface element 1905. Second drive assembly interface element 2101 is configured to receive second instrument interface element 1906. Third drive assembly interface element 2102 is configured to receive third instrument interface element 1907.

Figure 24:
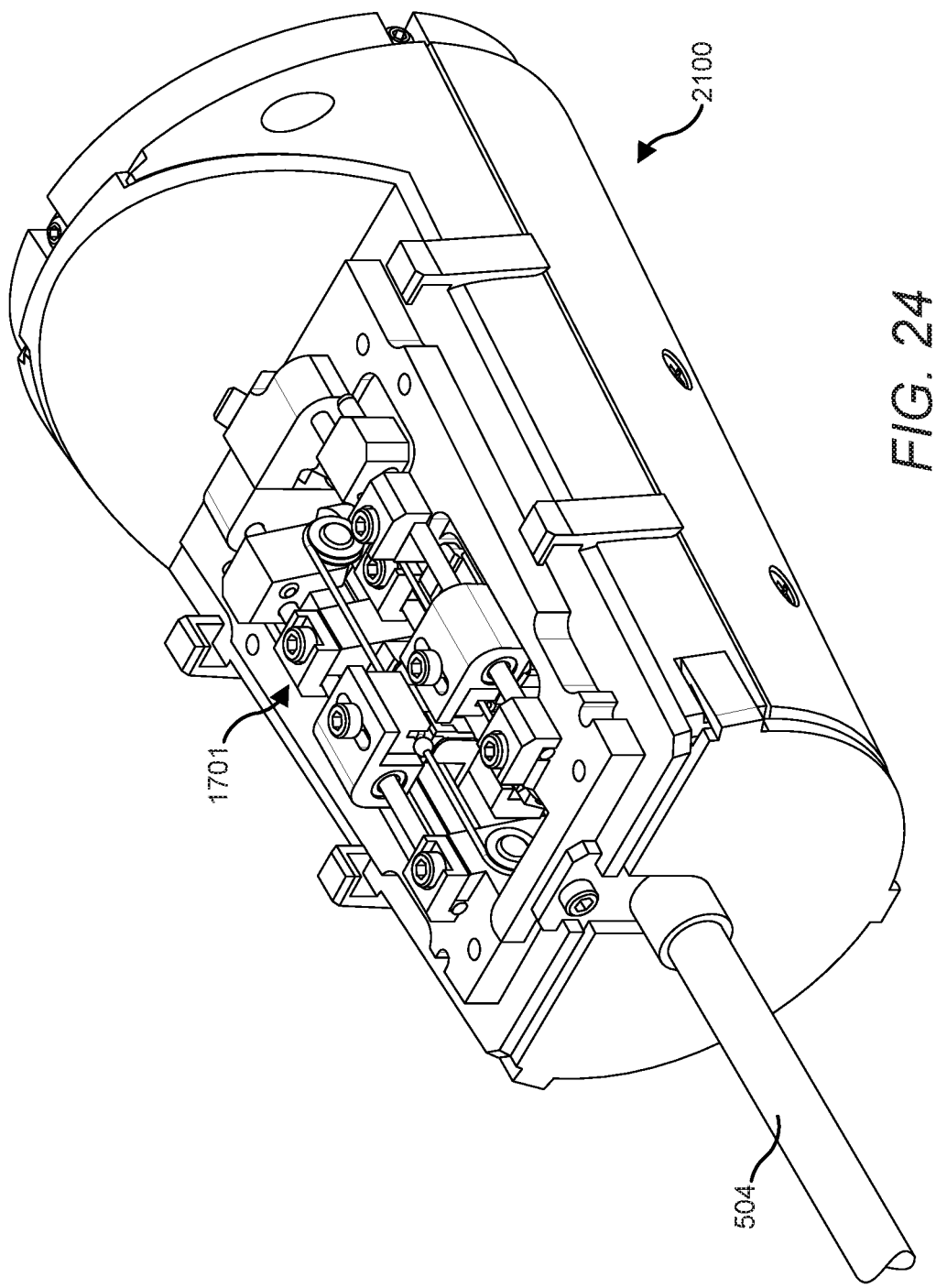
FIG. 24 illustrates an instrument interface engaged in a drive assembly interface.

Each drive assembly interface element is displaceable along a direction parallel to the longitudinal axis 2104 of the drive assembly. Each drive assembly interface element is displaceable over a displacement range. When the instrument interface 1701, for example as described above with respect to FIG. 19*c*, is seated in the drive assembly 2100, as shown in FIG. 24, each drive assembly interface element, for example as described above with respect to FIGS. 21*a*, 21*b*, and 21*c*, is displaceable in the same direction as the direction in which the instrument interface element that it engages with is displaceable in.

The first drive assembly interface element 2102 engages the first instrument interface element 1905 on the longitudinal axis 2104 of the drive assembly. Thus, the first drive assembly interface element 1905 drives the first instrument interface element 1905 a long the longitudinal axis of the drive assembly, and hence along the longitudinal axis of the terminal link of the robot arm. Suitably, of all the drive assembly interface elements in the drive assembly, only the first drive assembly interface element 2102 is displaceable along the longitudinal axis 2104 of the terminal link. The first instrument interface element 1905 drives the first pair of driving elements A1, A2 to drive rotation of the distal end of the instrument about the first axis 510 which is perpendicular to the instrument shaft axis 511. When the instrument interface 1701 is seated in the drive assembly 2100, the longitudinal axis 511 of the instrument shaft is parallel to the longitudinal axis 2104 of the terminal link. Suitably, the longitudinal axis 511 of the instrument shaft is coincident with the longitudinal axis 2104 of the terminal link.

The second drive assembly interface element 2101 engages the second instrument interface element 1906 on an axis parallel to but offset from the longitudinal axis 2104 of the drive assembly. The second drive assembly interface element 2101 is displaceable along this axis so as to drive the second instrument interface element 1906 along this axis. The second instrument interface element 1906 drives the second pair of driving elements B1, B2 to drive rotation of an end effector element 502 about the second joint 507.

The third drive assembly interface element 2103 engages the third instrument interface element 1907 on an axis parallel to but offset from the longitudinal axis 2104 of the drive assembly. The third drive assembly interface element 2103 is displaceable along this axis so as to drive the third instrument interface element 1907 along this axis. The third instrument interface element 1907 drives the third pair of driving elements C1, C2 to drive rotation of the end effector element 503 about the third joint 513.

Suitably, the drive assembly interface elements releasably engage the corresponding instrument interface elements.

FIGS. 21*a*, 21*b* and 21*c* illustrate an exemplary mechanism for driving the linear displacement of the drive assembly interface elements within the drive assembly. Each drive assembly interface element 2101, 2102, 2103 is driven by a respective threaded driveshaft 2105, 2106, 2107. Suitably, the first, second and third drive assembly interface elements are independently driven by the driveshafts. A guide structure constrains each drive assembly interface element, thereby preventing the drive assembly interface element from rotating as the corresponding driveshaft is rotated. For example, a guiderail constrains each drive assembly interface element, thereby preventing the drive assembly interface element from rotating as the corresponding driveshaft is rotated. The guiderails constrain the drive assembly interface elements such that the only motion that the drive assembly interface elements are permitted to do is to move linearly parallel to the guiderail. The drive assembly interface elements may, for example, slide along the guiderails. In the implementation illustrated, the first drive assembly interface element 2102 and the second drive assembly interface element 2101 are both constrained by the same guiderail 2108. The third drive assembly interface element 2103 is constrained by a different guiderail 2109. In an alternative arrangement, the first and third drive assembly interface elements 2102 and 2103 are both constrained by the same guiderail 2109. The second drive assembly interface element 2101 is constrained by the guiderail 2108. In yet a further alternative arrangement, each drive assembly interface element is constrained by its own guiderail. In another example, the guide structure is a guide slot, which constrains the motion of the drive assembly interface element such that it is only able to move linearly parallel to the guide slot. As with the guiderails, the guide slots are parallel to the longitudinal direction 2104 of the drive assembly interface. The first drive assembly interface element 2102 is linearly displaceable through a maximum distance $s_1$. The second drive assembly interface element 2101 is linearly displaceable through a maximum distance $s_2$. The third drive assembly interface element 2103 is linearly displaceable through a maximum distance $s_3$. Suitably $s_1 < s_2$ and $s_1 < s_3$. Suitably, $s_2 = s_3$.

Suitably, in one configuration of the drive assembly, the first, second and third drive assembly interface elements 2101, 2102 and 2103 are all located in the same plane perpendicular to the longitudinal axis 2104 of the terminal link. This configuration is the one depicted in FIGS. 21*a*, 21*b* and 21*c*. All the drive assembly interface elements are centred on a single cross section of the terminal link perpendicular to the longitudinal axis 2104. Suitably, in this configuration, each drive assembly interface element is at the midpoint of its linear displacement over its displacement range. Suitably, this configuration is the default configuration that the assembly interface adopts when an instrument has been removed from the robot arm. This configuration is arranged to receive the instrument interface elements in their predetermined alignment positions, described above. The predetermined alignment position may be the position at which each drive assembly interface element is at the midpoint of its travel. The predetermined alignment position may be the position at which the centre points of all the drive assembly interface elements lie on the same plane.

In all configurations of the drive assembly, the second and third drive assembly interface elements 2101 and 2103 are both centred on a second plane which is perpendicular to the plane that the first, second and third drive assembly interface elements 2102, 2102 and 2103 are all centred on in the configuration depicted in FIGS. 21*a*, 21*b* and 21*c*. This second plane does not intersect the longitudinal axis 2104 of the terminal link. In all configurations, the first drive assembly interface element 2102 is centred on a third plane which is parallel to but offset from the second plane.

The drive assembly depicted in FIGS. 21a, 21b and 21c may drive the instrument interface depicted in FIGS. 19a, 19b and 19c which in turn drives the first, second and third joints depicted in FIGS. 5a and 5b, such that the first drive assembly interface element 2102 drives the first joint 506, the second drive assembly interface element 2101 drives the second joint 507, and the third drive assembly interface element 2103 drives the third joint 513. In an alternative arrangement, the drive assembly interface elements may drive different joints. For example, if the first pair of driving elements A1, A2 are connected to the second instrument interface element 1906, then the second drive assembly interface element 2101 drives the first joint 506. If the second pair of driving elements B1, B2 are connected to the first instrument interface element 1905, then the first drive assembly interface element 2102 drives the second joint 507. In this example, the third pair of driving elements C1, C2 are connected to the third instrument interface element 1907, so that the third drive assembly interface element 2103 drives the third joint 513. In this example, the first drive assembly interface element 2102 is linearly displaceable through a maximum distance $s_1$. The second drive assembly interface element 2101 is linearly displaceable through a maximum distance $s_2$. The third drive assembly interface element 2103 is linearly displaceable through a maximum distance $s_3$. Suitably $s_2<s_1$ and $s_2<s_3$. Suitably, $s_1=s_3$.

Each instrument interface element comprises a body which is receivable in a corresponding socket of the drive assembly interface element. The shapes of the body and socket correspond such that when the drive assembly interface element is displaced, this displacement is transferred to the instrument interface element without any slippage. Thus, the body fits snugly into the socket along at least one line in the displacement direction. Suitably, the instrument interface element is displaceable over the same displacement range as its corresponding drive assembly interface element.

Figure 22A:
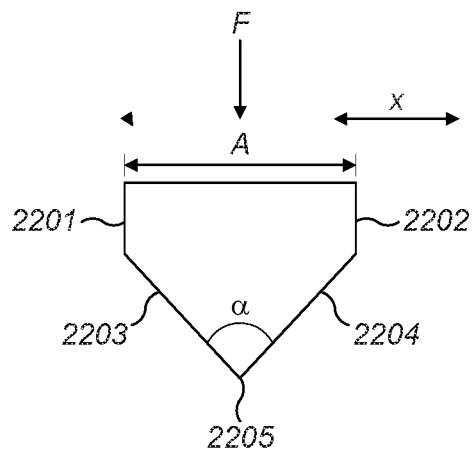
FIGS. 22a, 22b and 22c illustrate configurations of an instrument interface element.

FIG. 22a illustrates an exemplary arrangement of the part of the body of the instrument interface element which is received in the socket of the drive assembly interface element.

The body comprises lower sidewalls 2201 and 2202 which are separated by the length of the body in the displaceable direction x. The lower sidewalls are perpendicular to the displaceable direction x of the body. Upper sidewalls 2203 and 2204 taper to a point 2205 from the lower sidewalls. Suitably, the upper sidewalls taper symmetrically to a point. On engaging the instrument interface with the drive assembly interface, the point 2205 is inserted into the drive assembly interface element first, followed by the rest of the upper sidewalls 2203, 2204 and finally the lower sidewalls 2201, 2202. The angle α at which the upper sidewalls meet is preferably less than or the same as 80°. By selecting α≤80°, the body will slide into the socket when force is applied in the direction F as long as the point is inside the socket, even if the body and socket are not fully aligned along the displaceable direction x. The direction F is perpendicular to the displaceable direction x. In other words, the direction F is perpendicular to the longitudinal axis of the shaft 504 and perpendicular to the longitudinal axis of the drive assembly.

Figure 22B:
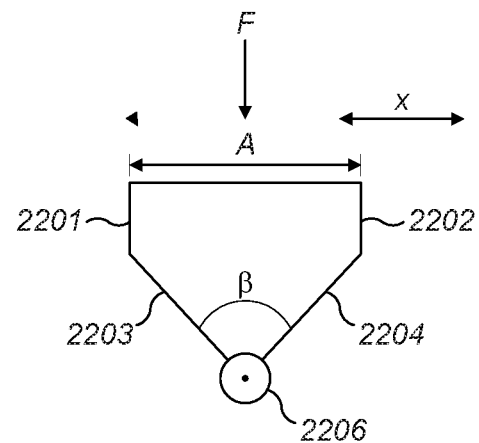

FIG. 22b illustrates another exemplary arrangement of the part of the body of the instrument interface which is received in the socket of the drive assembly of the drive assembly interface element. The body is the same as that described with reference to FIG. 22a except that it has a roller 2206 located on the point at which the two upper sidewalls meet. The roller 2206 is configured to rotate about an axis which is perpendicular to the displaceable direction x. The angle β at which the upper sidewalls meet may be greater than 80°. This is because the roller 2206 aids seating of the body in the socket even if the body and socket are not fully aligned along the displaceable direction x when force is applied in the direction F.

Figure 22C:
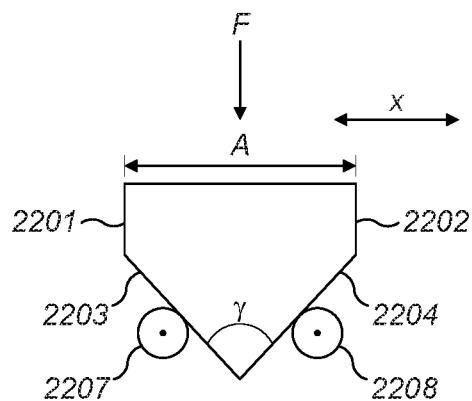

FIG. 22c illustrates another exemplary arrangement of the part of the body of the instrument interface which is received in the socket of the drive assembly of the drive assembly interface element. The body is the same as that described with reference to FIG. 22a except that it has a roller 2207, 2208 located on each upper sidewall. The rollers 2207, 2208 are configured to rotate about axes which are perpendicular to the displaceable direction x. The angle γ at which the upper sidewalls meet may be greater than 80°. This is because the rollers 2207, 2208 aid seating of the body in the socket even if the body and socket are not fully aligned along the displaceable direction x when force is applied in the direction F.

Figure 23:
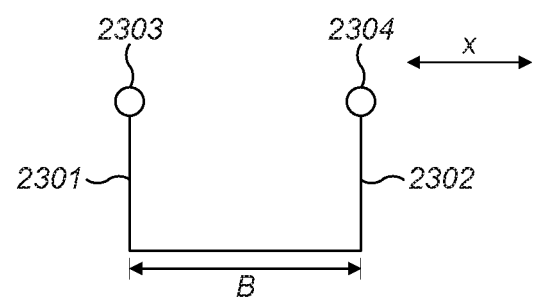
FIG. 23 illustrates a configuration of a drive assembly interface element.

FIG. 23 illustrates an exemplary arrangement of a socket of a drive assembly interface element. The body comprises sidewalls 2301 and 2302 which are separated by the length of the body in the displaceable direction x. The sidewalls are perpendicular to the displaceable direction x of the body. The sidewalls each terminate in a roller 2303, 2304. The rollers 2303, 2304 are configured to rotate about axes which are perpendicular to the displaceable direction x. The rollers 2303, 2304 aid seating of the body in the socket even if the body and socket are not fully aligned along the displaceable direction x when the instrument interface is applied to the drive assembly interface.

In one example, the length A of the body in the displaceable direction x is greater than the maximum distance the body is able to travel over the displacement range in the displaceable direction x. Suitably, the length A of the body in the displaceable direction x is greater than the maximum distance the socket of the drive assembly interface element is able to travel over its displacement range in the displaceable direction. Thus, whatever displacement position the body has and whatever displacement position the socket has, when the instrument interface is brought into engagement with the drive assembly interface, the body seats into the socket. Thus, no pre-alignment of the instrument interface elements and the drive assembly interface elements is required to cause the instrument interface and the drive assembly interface to mate. Suitably, the maximum distance the body is able to travel over its displacement range is half the length of the body A/2. A is the length of the body. Suitably, the maximum distance the socket is able to travel over its displacement range is half the length of the body A/2.

In one example, the length B of the socket in the displaceable direction x is greater than the maximum distance the body is able to travel over the displacement range in the displaceable direction x. Suitably, the length B of the socket in the displaceable direction x is greater than the maximum distance the socket of the drive assembly interface element is able to travel over its displacement range in the displaceable direction. Thus, whatever displacement position the body has and whatever displacement position the socket has, when the instrument interface is brought into engagement with the drive assembly interface, the body seats into the socket. Thus, no pre-alignment of the instrument interface elements and the drive assembly interface elements is required to cause the instrument interface and the drive assembly interface to mate. Suitably, the maximum distance the body is able to travel over its displacement range is half the length of the socket B/2. B is the length of the socket. Suitably, the maximum distance the socket is able to travel over its displacement range is half the length of the socket B/2.

Suitably, the length A of the body in the displaceable direction is equal to the length B of the socket in the displaceable direction.

The instrument interface may have a guide bar to aid alignment and seating of the instrument interface into the drive assembly interface when they are being brought into engagement. The guide bar is located on the exterior face of the instrument interface which faces the drive assembly interface when they are brought into engagement. The guide bar is received in the drive assembly interface prior to the instrument interface elements. Suitably, the guide bar is the first part of the instrument interface to be received in the drive assembly interface as they are brought into contact with each other. Once the guide bar has been received in the drive assembly interface, it constrains the relative orientation with which the instrument interface and drive assembly interface are able to engage so as to align their longitudinal attitudes. Suitably, the guide bar only permits the instrument interface to seat fully into the drive assembly interface if the longitudinal axis 511 of the instrument shaft is aligned with the longitudinal axis 2104 of the terminal link of the robot arm.

Suitably, the guide bar is elongate, straight and parallel to the longitudinal axis 511 of the instrument shaft. The guide bar may extend wholly across the instrument interface. For example, the guide bar may extend in the longitudinal direction x from the end of the instrument interface which abuts the instrument shaft 504 to the opposing end of the instrument interface. Alternatively, the guide bar may extend in the longitudinal direction x only over the longitudinal range bounded by the minimum and maximum displacement positions of the 1931, 1932 of the instrument interface elements 1905, 1906, 1907. If the drive assembly interface and instrument interface are arranged such that they both adopt their default predetermined alignment positions before being brought into engagement, then the guide bar may extend in the longitudinal direction x only over the longitudinal range bounded by the displacements of the instrument interface elements in the predetermined alignment positions. If in the predetermined alignment positions, the instrument interface elements are all aligned in the same plane perpendicular to the longitudinal axis 511 of the instrument shaft, then the guide bar may extend in the longitudinal direction x only over the instrument interface elements themselves. Suitably, the guide bar is narrower than the diameter of the instrument shaft 504. The drive assembly receives the guide bar parallel to the longitudinal axis 2104 of the drive assembly.

The guide bar may be formed of a single part, such as guide bar 1960 shown in FIG. 19a. This illustrated guide bar extends across the whole length of the instrument interface. The guide bar partially or wholly envelops driving elements A1, A2, B1 and C1. In this way, the driving elements are not exposed at the exterior of the instrument interface as the instrument interface is brought into engagement with the drive assembly interface. The guide bar 1960 also stiffens the instrument interface.

Figure 25:
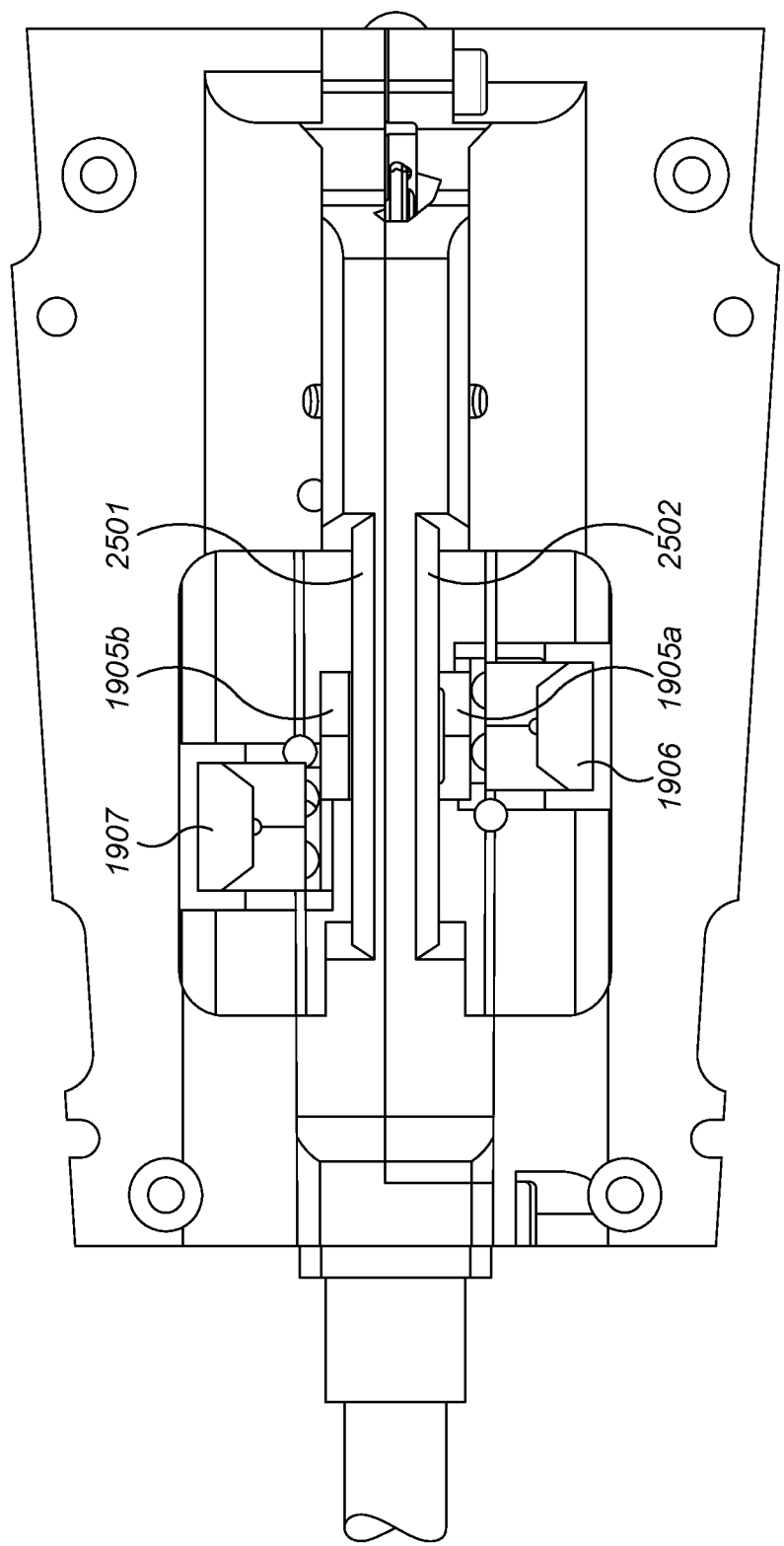
FIG. 25 illustrates a further view of an instrument interface.

Alternatively, the guide bar may comprise two or more parts. FIG. 25 shows a view of the face of an instrument interface which first engages with the drive assembly interface. Here, two guide bar parts 2501, 2502 are shown. This guide bar extends in the longitudinal direction x across part of the longitudinal range bounded by the minimum and maximum displacement positions of the instrument interface elements.

Both the guide bar and the first instrument interface element 1905 are received in the first drive assembly interface element 2102. The first instrument interface element comprises two body parts 1905a and 1905b, one of which is located on one side of the guide bar, and the other of which is located on an opposing side of the guide bar. The first drive assembly interface element comprises two socket parts 2101a and 2101b, located on either side of the longitudinal axis 2104 of the drive assembly. As the instrument interface and the drive assembly interface are brought into engagement, the guide bar is received in the first drive assembly interface element first. The guide bar seats along the longitudinal axis 2104 of the shaft between the two socket parts 2101a and 2101b. As the guide bar is received in the first drive assembly interface element 2101, it prevents the instrument interface from twisting as it is located in the drive assembly interface. The guide bar causes the attitudes of the drive assembly interface and the instrument interface to remain aligned as they engage. As the instrument interface is further lowered into the drive assembly interface, the first body part 1905a engages the first socket part 2101a on one side of the guide bar whilst the second body part 1905b engages the second socket part 2101b on the opposing side of the guide bar.

It will be appreciated that the drive assembly interfaces described herein could be modified to include further drive assembly interface elements to transfer drive to further instrument interface elements. The instrument interfaces described herein could be modified to include further instrument interface elements to transfer drive to further joints of the articulation at the distal end of the instrument shaft. The articulation itself could also be modified to include further joints.

It will also be appreciated that the end effector may only have one end effector element. In this case, the articulation does not include the third joint 513, the instrument interface does not include an instrument interface element for driving the third joint, and the drive assembly does not include a drive assembly interface element for driving that instrument interface element.

The instrument could be used for non-surgical purposes. For example it could be used in a cosmetic procedure.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

The invention claimed is:

1. A robotic surgical instrument having a proximal end configured to engage with a surgical robot arm, the robotic surgical instrument comprising:
    a shaft;
    an articulation at a distal end of the shaft configured to articulate an end effector, the articulation driveable by a pair of driving elements; and an instrument interface at a proximal end of the shaft, the instrument interface comprising an instrument interface element configured to drive the pair of driving elements, the instrument interface element displaceable in a displaceable direction over a first displacement range, the instrument interface element comprising a body receivable in a drive assembly interface element of the surgical robot arm when the proximal end of the robotic surgical instrument engages with the surgical robot arm, the drive assembly interface element displaceable in the displaceable direction over a second displacement range, a length of the body in the displaceable direction being greater than one of a maximum travel of the body over the first displacement range and a maximum travel of the drive assembly interface element over the second displacement range.

2. A robotic surgical instrument as claimed in claim 1, wherein the length of the body in the displaceable direction is greater than both the maximum travel of the body over the first displacement range and the maximum travel of the drive assembly interface element over the second displacement range.

3. A robotic surgical instrument as claimed in claim 1, wherein the first displacement range is the same as the second displacement range.

4. A robotic surgical instrument as claimed in claim 1, wherein the second displacement range is parallel to the first displacement range.

5. A robotic surgical instrument as claimed in claim 1, wherein the first displacement range is parallel to a longitudinal axis of the shaft.

6. A robotic surgical instrument as claimed in claim 1, wherein the body comprises:
lower sidewalls separated by the length of the body in the displaceable direction; and
upper sidewalls which taper from the lower sidewalk.

7. A robotic surgical instrument as claimed in claim 6, wherein the upper sidewalls taper to a point.

8. A robotic surgical instrument as claimed in claim 7, wherein the upper sidewalls taper to a point meeting at an angle of less than or the same as 80°.

9. A robotic surgical instrument as claimed in claim 6, wherein the upper sidewalls taper from the lower sidewalls to a roller, the roller configured to rotate about an axis perpendicular to the displaceable direction.

10. A robotic surgical instrument as claimed in claim 6, comprising a roller attached to each upper sidewall, each roller configured to rotate about an axis perpendicular to the displaceable direction.

11. A robotic surgical instrument as claimed in claim 6, wherein the lower sidewalk are perpendicular to the displaceable direction.

12. A robotic surgical instrument as claimed in claim 1, wherein the maximum travel of the body over the first displacement range is half the length of the body, and wherein maximum travel of the drive assembly interface element over the second displacement range is half the length of the body.

13. A surgical robot arm configured to engage with a proximal end of a robotic surgical instrument, the surgical robot arm comprising:
a drive assembly at a distal end of the surgical robot arm, the drive assembly comprising a drive assembly interface element configured to drive an instrument interface element of the robotic surgical instrument when the surgical robot arm engages with the proximal end of the robotic surgical instrument, the drive assembly interface element comprising a socket configured to receive a body of the instrument interface element, the instrument interface element displaceable in a displaceable direction over a first displacement range and the drive assembly interface element displaceable in the displaceable direction over a second displacement range, an internal length of the socket in the displaceable direction being greater than one of a maximum travel of the body over the first displacement range and a maximum travel of the socket over the second displacement range.

14. A surgical robot arm as claimed in claim 13, wherein the length of the socket in the displaceable direction is greater than both the maximum travel of the body over the first displacement range and the maximum travel of the socket over the second displacement range.

15. A surgical robot arm as claimed in claim 13, wherein the first displacement range is the same as the second displacement range.

16. A surgical robot arm as claimed in-claim 13, wherein the first displacement range is parallel to the second displacement range.

17. A surgical robot arm as claimed in claim 13, wherein the socket comprises sidewalls separated by the length of the body in the displaceable direction, the sidewalls each terminating in a roller, each roller configured to rotate about an axis perpendicular to the displaceable direction.

18. A surgical robot arm as claimed in claim 17, wherein the sidewalk are perpendicular to the displaceable direction.

19. A surgical robot arm as claimed in claim 13, wherein the maximum travel of the socket over the second displacement range is half the length of the socket, and the maximum travel of the body over the first displacement range is half the length of the socket.

20. A surgical robot comprising:
a robotic surgical instrument comprising:
a shaft;
an articulation at a distal end of the shaft configured to articulate an end effector, the articulation driveable by a pair of driving elements; and
an instrument interface at a proximal end of the shaft, the instrument interface comprising an instrument interface element configured to drive the pair of driving elements, the instrument interface element displaceable in a displaceable direction over a first displacement range, the instrument interface element comprising a body; and
a surgical robot arm comprising a drive assembly at a distal end of the surgical robot arm, the drive assembly comprising a drive assembly interface element configured to drive the instrument interface element when the surgical robot arm engages with a proximal end of the robotic surgical instrument, the drive assembly interface element displaceable in the displaceable direction over a second displacement range, the drive assembly interface element comprising a socket configured to receive the body;
wherein a length of the body in the displaceable direction is greater than one of a maximum travel of the body over the first displacement range and a maximum travel of the drive assembly interface element over the second displacement range.

* * * * *